US012686877B2

(12) United States Patent
Hillmann et al.

(10) Patent No.: US 12,686,877 B2
(45) Date of Patent: Jul. 21, 2026

(54) METHOD FOR PRODUCING OLIVETOLIC ACID IN AN AMOEBOZOA HOST SPECIES

(71) Applicant: LEIBNIZ-INSTITUT FÜR NATURSTOFF-FORSCHUNG UND INFEKTIONSBIOLOGIE E. V. HANS-KNÖLL-INSTITUTE (HKI), Jena (DE)

(72) Inventors: Falk Hillmann, Jena (DE); Christin Reimer, Jena (DE); Johann Elias Kufs, Jena (DE); Vito Valiante, Jena (DE)

(73) Assignee: Leibniz-Institut für Naturstoff-Forschung und Infektionsbiologie e. V. Hans-Knöll-Institut (HKI), Jena (DE)

( * ) Notice: Subject to any disclaimer, the term of this patent is extended or adjusted under 35 U.S.C. 154(b) by 637 days.

(21) Appl. No.: 18/013,082

(22) PCT Filed: Jul. 1, 2021

(86) PCT No.: PCT/EP2021/068240

§ 371 (c)(1),
(2) Date: Dec. 27, 2022

(87) PCT Pub. No.: WO2022/003126

PCT Pub. Date: Jan. 6, 2022

(65) Prior Publication Data

US 2023/0272439 A1 Aug. 31, 2023

(30) Foreign Application Priority Data

Jul. 3, 2020 (DE) .................... 10 2020 117 610.4

(51) Int. Cl.
| | |
|---|---|
| *C12P 7/42* | (2006.01) |
| *C12N 1/11* | (2006.01) |
| *C12N 9/10* | (2006.01) |
| *C12N 9/88* | (2006.01) |
| *C12N 15/52* | (2006.01) |
| *C12N 15/79* | (2006.01) |

(52) U.S. Cl.
CPC .............. *C12P 7/42* (2013.01); *C12N 9/1029* (2013.01); *C12N 9/88* (2013.01); *C12N 15/52* (2013.01); *C12N 15/79* (2013.01); *C12Y 203/01206* (2015.07); *C12Y 404/01026* (2015.07)

(58) Field of Classification Search
None
See application file for complete search history.

(56) References Cited

U.S. PATENT DOCUMENTS

2008/0233628 A1 9/2008 Austin et al.
2022/0259603 A1* 8/2022 Bourgeois .............. C12P 17/04

FOREIGN PATENT DOCUMENTS

WO 2011/127589 A1 10/2011
WO 2018/148848 A1 8/2018
WO 2019/210404 A1 11/2019

OTHER PUBLICATIONS

Veltman et al., A new set of small, extrachromosomal expression vectors for Dictyostelium discoideum, Plasmid 61, 2009, 110-18 (Year: 2009).*
Hoefgen et al., Facile assembly and fluorescence-based screening method for heterologous expression of biosynthetic pathways in fungi, Metabolic Eng. 48, 2018, 44-51. (Year: 2018).*
Arya, Ranjana et al. "Dictyostelium discoideum-a promising expression system for the production of eukaryotic proteins." The FASEB Journal 22(12):4055-4066, (Year: 2008).
Tan, Zaigao et al. "Synthetic Pathway for the Production of Olivetolic Acid in *Escherichia coli*." ACS Synthetic Biology 7(8):1886-1896, Jul. 5, 2018.
Taura, Futoshi et al. "Characterization of olivetol synthase, a polyketide synthase putatively involved in cannabinoid biosynthetic pathway." FEBS letters 583(12):2061-2066, (Year: 2009).
Austin, Michael B. "Biosynthesis of Dictyostelium discoideum differentiation-inducing factor by a hybrid type I fatty acid-type III polyketide synthase." Nature chemical biology 2(9):494-502, (Year: 2006).

* cited by examiner

*Primary Examiner* — Todd M Epstein
(74) *Attorney, Agent, or Firm* — SALIWANCHIK, LLOYD & EISENSCHENK

(57) ABSTRACT

The present invention relates to a method for the recombinant production of olivetolic acid (OA) in a host species selected from amoebozoa, based on a hybrid-gene or enzyme of polyketide synthase 37 (PKS37) in which the C-terminal type III PKS domain from an amoeba is replaced by an olivetol synthase (OLS) from a plant, and is expressed together with an olivetolic acid cyclase from a multi-gene expression vector. Further provided is a recombinant amoebozoa host species, and an improved method for producing $\Delta^9$-tetrahydrocannabinol (THC) or other cannabinoids.

11 Claims, 9 Drawing Sheets

Figure 1:
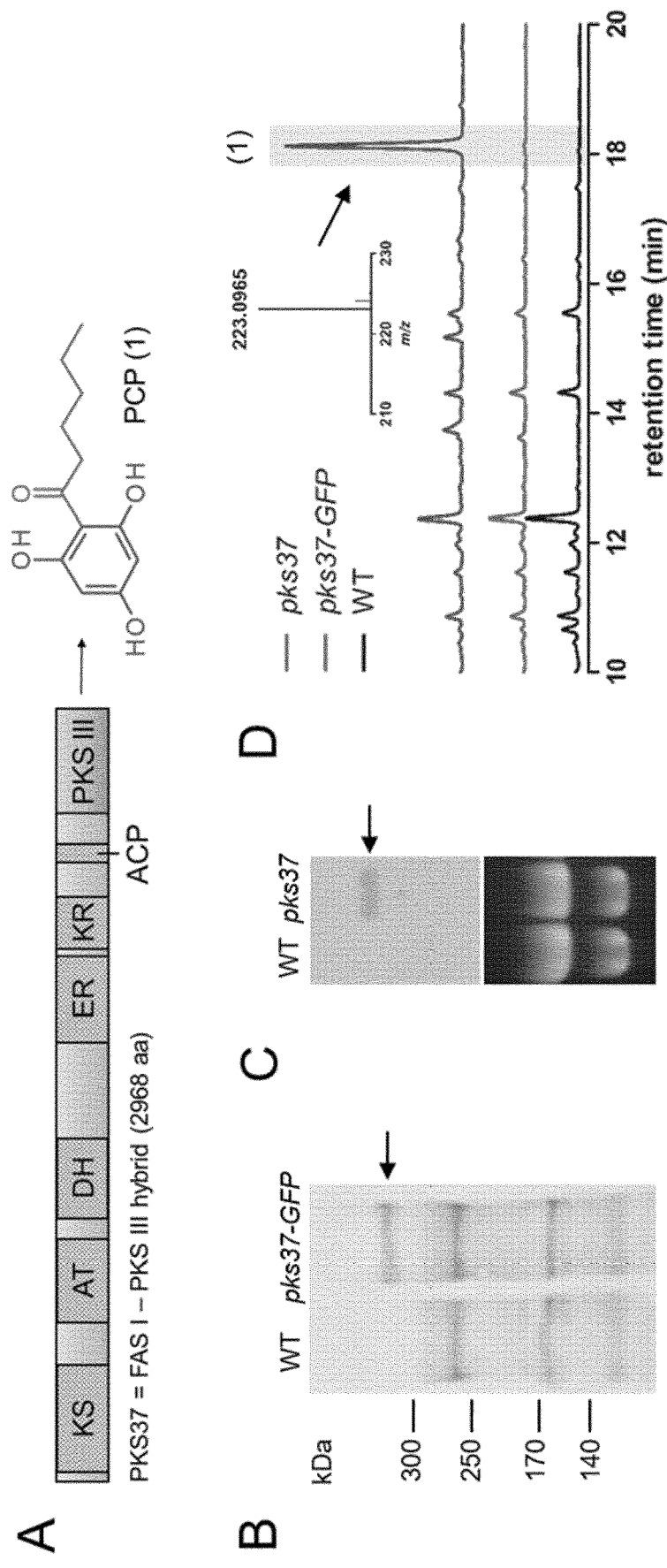
Figure 1:
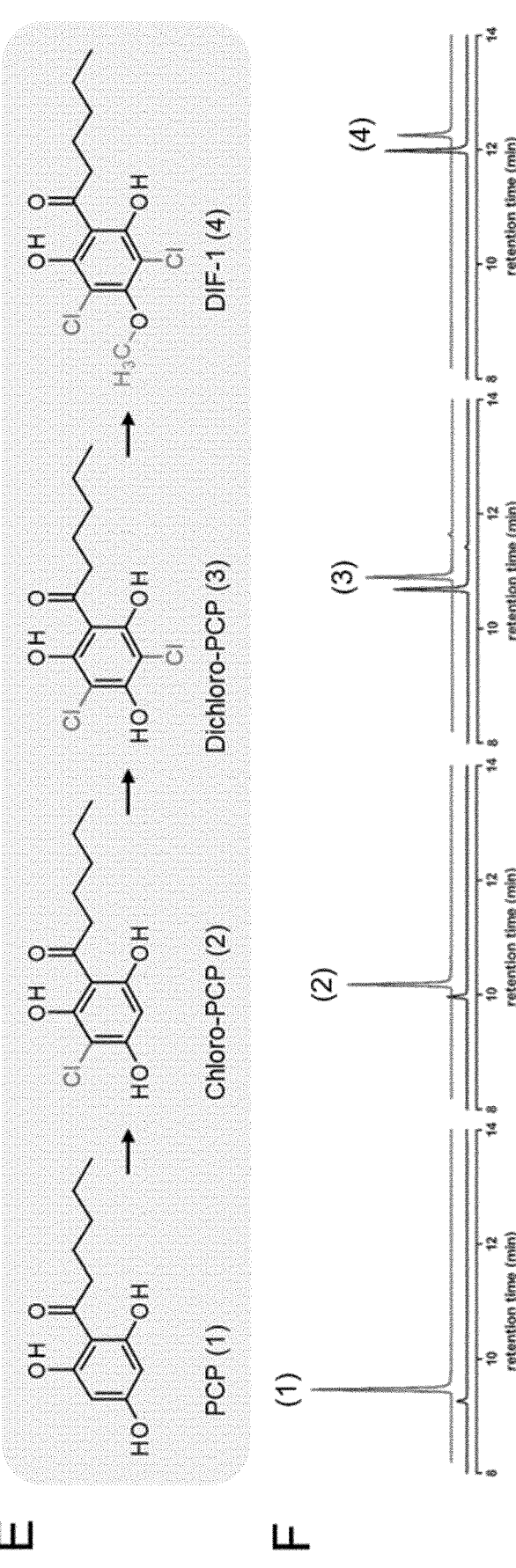

Specification includes a Sequence Listing.

SEQUENCE LISTING

<160> NUMBER OF SEQ ID NOS: 50

<210> SEQ ID NO 1
<211> LENGTH: 54
<212> TYPE: DNA
<213> ORGANISM: Dictyostelium discoideum

<400> SEQUENCE: 1
aaaaataaaa atcagatcca agcttaaaaa atgaacaaca acaaaagtat aaac          54

<210> SEQ ID NO 2
<211> LENGTH: 54
<212> TYPE: DNA
<213> ORGANISM: Dictyostelium discoideum

<400> SEQUENCE: 2
aactccagtg aaaagttctt ctcctttact tttaattaat ttaaataaaa ttgc          54

<210> SEQ ID NO 3
<211> LENGTH: 27
<212> TYPE: DNA
<213> ORGANISM: artificial sequence

```
<220> FEATURE:
<223> OTHER INFORMATION: pTX-GFP

<400> SEQUENCE: 3
agtaaaggag aagaactttt cactgga                                    27

<210> SEQ ID NO 4
<211> LENGTH: 30
<212> TYPE: DNA
<213> ORGANISM: artificial sequence
<220> FEATURE:
<223> OTHER INFORMATION: pTX-GFP

<400> SEQUENCE: 4
tttttaagct tggatctgat ttttattttt                                 30

<210> SEQ ID NO 5
<211> LENGTH: 54
<212> TYPE: DNA
<213> ORGANISM: Dictyostelium discoideum

<400> SEQUENCE: 5
gaattcctgc agcccggggg atcgtctaga ttatttaatt aatttaaata aaat       54

<210> SEQ ID NO 6
<211> LENGTH: 36
<212> TYPE: DNA
<213> ORGANISM: artificial sequence
<220> FEATURE:
<223> OTHER INFORMATION: pTX

<400> SEQUENCE: 6
aaattaatta ataatctag acgatccccc gggctg                           36

<210> SEQ ID NO 7
<211> LENGTH: 45
<212> TYPE: DNA
<213> ORGANISM: artificial sequence
<220> FEATURE:
<223> OTHER INFORMATION: pTX

<400> SEQUENCE: 7
tttgttgttg ttcatttttt aagcttggat ctgattttta ttttt               45

<210> SEQ ID NO 8
<211> LENGTH: 18
<212> TYPE: DNA
<213> ORGANISM: artificial sequence
<220> FEATURE:
<223> OTHER INFORMATION: pTX

<400> SEQUENCE: 8
tctagacgat cccccggg                                              18

<210> SEQ ID NO 9
<211> LENGTH: 57
<212> TYPE: DNA
<213> ORGANISM: Dictyostelium discoideum

<400> SEQUENCE: 9
aaaaataaaa atcagatcca agcttaaaaa atgaataaaa attcaaaaat ccaatca    57

<210> SEQ ID NO 10
<211> LENGTH: 57
<212> TYPE: DNA
```

-continued

<213> ORGANISM: Dictyostelium discoideum

<400> SEQUENCE: 10
gaattcctgc agcccggggg atcgtctaga ttagacaaca tttttaaga aacaacc          57

<210> SEQ ID NO 11
<211> LENGTH: 57
<212> TYPE: DNA
<213> ORGANISM: Dictyostelium discoideum

<400> SEQUENCE: 11
aaaaataaaa atcagatcca agcttaaaaa atggatatga aattaaatga tattgaa          57

<210> SEQ ID NO 12
<211> LENGTH: 60
<212> TYPE: DNA
<213> ORGANISM: Dictyostelium discoideum

<400> SEQUENCE: 12
gaattcctgc agcccggggg atcgtctaga ttatttattt atctttttca aaaaatttaa       60

<210> SEQ ID NO 13
<211> LENGTH: 58
<212> TYPE: DNA
<213> ORGANISM: Dictyostelium discoideum

<400> SEQUENCE: 13
aaaaataaaa atcagatcca agcttaaaaa atggaaaact ttaaatatag aaataatg         58

<210> SEQ ID NO 14
<211> LENGTH: 50
<212> TYPE: DNA
<213> ORGANISM: Dictyostelium discoideum

<400> SEQUENCE: 14
gaattcctgc agcccggggg atcgtctaga ttattcttgg ctttgaactt                  50

<210> SEQ ID NO 15
<211> LENGTH: 36
<212> TYPE: DNA
<213> ORGANISM: artificial sequence
<220> FEATURE:
<223> OTHER INFORMATION: pTX

<400> SEQUENCE: 15
acggttacaa attaatctag acgatccccc gggctg                                 36

<210> SEQ ID NO 16
<211> LENGTH: 45
<212> TYPE: DNA
<213> ORGANISM: artificial sequence
<220> FEATURE:
<223> OTHER INFORMATION: pTX

<400> SEQUENCE: 16
ctcaactgaa gccatttttt aagcttggat ctgatttta ttttt                        45

<210> SEQ ID NO 17
<211> LENGTH: 54
<212> TYPE: DNA
<213> ORGANISM: Vitis vinifera

<400> SEQUENCE: 17
aaaaataaaa atcagatcca agcttaaaaa atggcttcag ttgaggaatt taga             54

```
<210> SEQ ID NO 18
<211> LENGTH: 54
<212> TYPE: DNA
<213> ORGANISM: Vitis vinifera

<400> SEQUENCE: 18
gaattcctgc agcccggggg atcgtctaga ttaatttgta accgtaggaa cgct          54

<210> SEQ ID NO 19
<211> LENGTH: 51
<212> TYPE: DNA
<213> ORGANISM: Escherichia coli

<400> SEQUENCE: 19
ggcgacgttg aagaaaaccc tggccctgat atgcatccca caggcccgca t             51

<210> SEQ ID NO 20
<211> LENGTH: 63
<212> TYPE: DNA
<213> ORGANISM: Escherichia coli

<400> SEQUENCE: 20
catcgcacct tgaaaataaa gattttcgat ttcaatctct tcacagacat cctgcgttaa    60
acg                                                                  63

<210> SEQ ID NO 21
<211> LENGTH: 54
<212> TYPE: DNA
<213> ORGANISM: Cannabis sativa

<400> SEQUENCE: 21
ggcgacgttg aagaaaaccc tggccctgat atgaatcatc ttcgtgctga gggt          54

<210> SEQ ID NO 22
<211> LENGTH: 54
<212> TYPE: DNA
<213> ORGANISM: Cannabis sativa

<400> SEQUENCE: 22
catcgcacct tgaaaataaa gattttcgat atatttgatg ggaacactac gcac          54

<210> SEQ ID NO 23
<211> LENGTH: 60
<212> TYPE: DNA
<213> ORGANISM: Cannabis sativa

<400> SEQUENCE: 23
ggcgacgttg aagaaaaccc tggccctgat atggcagtga agcatttgat tgtattgaag    60

<210> SEQ ID NO 24
<211> LENGTH: 60
<212> TYPE: DNA
<213> ORGANISM: Cannabis sativa

<400> SEQUENCE: 24
catcgcacct tgaaaataaa gattttcgat ctttcgtggt gtgtagtcaa aaatgagaag    60

<210> SEQ ID NO 25
<211> LENGTH: 59
<212> TYPE: DNA
<213> ORGANISM: artificial sequence
<220> FEATURE:
```

-continued

<223> OTHER INFORMATION: Venus-TEV

<400> SEQUENCE: 25
taaattaaat taaataaaaa ataaaaatca aaaaaatgga taaagcggaa ttaattccc          59

<210> SEQ ID NO 26
<211> LENGTH: 50
<212> TYPE: DNA
<213> ORGANISM: artificial sequence
<220> FEATURE:
<223> OTHER INFORMATION: Venus-TEV

<400> SEQUENCE: 26
ttaaataatt tatttattta actagtacta ctacttgtac agctcgtcca                    50

<210> SEQ ID NO 27
<211> LENGTH: 31
<212> TYPE: DNA
<213> ORGANISM: artificial sequence
<220> FEATURE:
<223> OTHER INFORMATION: pDM310_Venus-TEV plasmid

<400> SEQUENCE: 27
atcgaaaatc tttattttca aggtgcgatg g                                        31

<210> SEQ ID NO 28
<211> LENGTH: 18
<212> TYPE: DNA
<213> ORGANISM: artificial sequence
<220> FEATURE:
<223> OTHER INFORMATION: pDM310_Venus-TEV plasmid

<400> SEQUENCE: 28
gtcgccgtca agctcgac                                                       18

<210> SEQ ID NO 29
<211> LENGTH: 21
<212> TYPE: DNA
<213> ORGANISM: artificial sequence
<220> FEATURE:
<223> OTHER INFORMATION: pChR2

<400> SEQUENCE: 29
gtggagcacg agatgcaaac t                                                   21

<210> SEQ ID NO 30
<211> LENGTH: 33
<212> TYPE: DNA
<213> ORGANISM: artificial sequence
<220> FEATURE:
<223> OTHER INFORMATION: pChR2

<400> SEQUENCE: 30
cgggcctgtg ggatgcattc tagatcaggg cca                                      33

<210> SEQ ID NO 31
<211> LENGTH: 62
<212> TYPE: DNA
<213> ORGANISM: Dictyostelium discoideum

<400> SEQUENCE: 31
ggcgacgttg aagaaaaccc tggccctgat atgaacaaca acaaaagtat aaacgattta         60
ag                                                                        62

```
<210> SEQ ID NO 32
<211> LENGTH: 45
<212> TYPE: DNA
<213> ORGANISM: Dictyostelium discoideum

<400> SEQUENCE: 32
aaactcatct tgtaaaattg gtgaaatttc ataaattact gttgc                45

<210> SEQ ID NO 33
<211> LENGTH: 45
<212> TYPE: DNA
<213> ORGANISM: Dictyostelium discoideum

<400> SEQUENCE: 33
agcacgaaga tgattaattg gtgaaatttc ataaattact gttgc                45

<210> SEQ ID NO 34
<211> LENGTH: 51
<212> TYPE: DNA
<213> ORGANISM: Dictyostelium discoideum

<400> SEQUENCE: 34
ggcggtgcca atggcatcgt tatcactatt attatcttct gatattattg g         51

<210> SEQ ID NO 35
<211> LENGTH: 40
<212> TYPE: DNA
<213> ORGANISM: Cannabis sativa

<400> SEQUENCE: 35
gaaatttcac caattttaca agatgagttt cctgactact                      40

<210> SEQ ID NO 36
<211> LENGTH: 36
<212> TYPE: DNA
<213> ORGANISM: Cannabis sativa

<400> SEQUENCE: 36
gaaatttcac caattaatca tcttcgtgct gagggt                          36

<210> SEQ ID NO 37
<211> LENGTH: 33
<212> TYPE: DNA
<213> ORGANISM: Cannabis sativa

<400> SEQUENCE: 37
aatagtgata acgatgccat tggcaccgcc aat                             33

<210> SEQ ID NO 38
<211> LENGTH: 21
<212> TYPE: DNA
<213> ORGANISM: Cannabis sativa

<400> SEQUENCE: 38
gatggccttt gcacaagcat c                                          21

<210> SEQ ID NO 39
<211> LENGTH: 39
<212> TYPE: DNA
<213> ORGANISM: Dictyostelium discoideum

<400> SEQUENCE: 39
gactatggtt tagatgcatt actatcaagt gaattatca                       39
```

-continued

```
<210> SEQ ID NO 40
<211> LENGTH: 39
<212> TYPE: DNA
<213> ORGANISM: Dictyostelium discoideum

<400> SEQUENCE: 40
cacttgatag taatgcatct aaaccatagt cactaaatg                             39

<210> SEQ ID NO 41
<211> LENGTH: 23
<212> TYPE: DNA
<213> ORGANISM: Cannabis sativa

<400> SEQUENCE: 41
ggagaaagct tgtttaaggg gcc                                             23

<210> SEQ ID NO 42
<211> LENGTH: 47
<212> TYPE: DNA
<213> ORGANISM: Cannabis sativa

<400> SEQUENCE: 42
agctctgaga tggttaattg gtgaaatttc ataaattact gttgcca                   47

<210> SEQ ID NO 43
<211> LENGTH: 37
<212> TYPE: DNA
<213> ORGANISM: Cannabis sativa

<400> SEQUENCE: 43
gaaatttcac caattaacca tctcagagct gaaggac                              37

<210> SEQ ID NO 44
<211> LENGTH: 32
<212> TYPE: DNA
<213> ORGANISM: Cannabis sativa

<400> SEQUENCE: 44
atatttaatt ggaactgatc taacaacaac tc                                   32

<210> SEQ ID NO 45
<211> LENGTH: 32
<212> TYPE: DNA
<213> ORGANISM: Cannabis sativa

<400> SEQUENCE: 45
gagttgttgt tagatcagtt ccaattaaat at                                   32

<210> SEQ ID NO 46
<211> LENGTH: 19
<212> TYPE: DNA
<213> ORGANISM: Cannabis sativa

<400> SEQUENCE: 46
atcacgcggc cccttaaac                                                  19

<210> SEQ ID NO 47
<211> LENGTH: 47
<212> TYPE: DNA
<213> ORGANISM: Dictyostelium discoideum

<400> SEQUENCE: 47
ggatcgtcta gattaatatt taattggaac tgatctaaca acaactc                   47
```

-continued

```
<210> SEQ ID NO 48
<211> LENGTH: 36
<212> TYPE: DNA
<213> ORGANISM: Dictyostelium discoideum

<400> SEQUENCE: 48
gttccaatta aatattaatc tagacgatcc cccggg                                    36

<210> SEQ ID NO 49
<211> LENGTH: 28
<212> TYPE: DNA
<213> ORGANISM: Dictyostelium discoideum

<400> SEQUENCE: 49
gccattagat tcatgtcatc cggtaatc                                             28

<210> SEQ ID NO 50
<211> LENGTH: 26
<212> TYPE: DNA
<213> ORGANISM: Dictyostelium discoideum

<400> SEQUENCE: 50
gccataccaa catcaggtat agaagc                                               26
```

METHOD FOR PRODUCING OLIVETOLIC ACID IN AN AMOEBOZOA HOST SPECIES

CROSS REFERENCE TO RELATED APPLICATIONS

This application is a National Stage Application of International Application Number PCT/EP2021/068240, filed Jul. 1, 2021; which claims priority to German Patent Application No. 10 2020 117 610.4, filed Jul. 3, 2020, both of which are incorporated herein by reference in their entirety.

The Sequence Listing for this application is labeled "SeqList-20Dec22-ST25.txt", which was created on Dec. 20, 2022 and is 9 KB. The entire content is incorporated herein by reference in its entirety.

The present invention relates to a method for the recombinant production of olivetolic acid (OA) in a host species selected from amoebozoa, based on a hybrid-gene or enzyme of polyketide synthase 37 (PKS37) in which the C-terminal type III PKS domain from an amoeba is replaced by an olivetol synthase (OLS) from a plant, and is expressed together with an olivetolic acid cyclase from a multi-gene expression vector. Further provided is a recombinant amoebozoa host species, and an improved method for producing 49-tetrahydrocannabinol (THC) or other cannabinoids.

BACKGROUND OF THE INVENTION

Polyketides are structurally and functionally diverse natural products, mainly derived from bacteria, fungi and plants, having a wide range of bioactivities with relevance as therapeutics (1-4). They are synthesized by condensation of Coenzyme A (CoA) esters by multi-domain enzymes or enzyme complexes, the polyketide synthases (PKSs).

PKSs are generally classified by their domain architecture and enzymatic mode of action (3). Type I PKSs partially resemble type I fatty acid synthases with a modular assembly of all catalytic domains on a large single polypeptide chain (5), while type II PKSs are multi-enzyme complexes of single subunits (6). Subtypes of both groups can either catalyze one round of elongation or function iteratively by incorporating further acyl-CoA units during multiple enzymatic cycles. Such iterative type I PKSs are widespread among filamentous fungi and can yield important therapeutics such as the cholesterol-lowering agent lovastatin or produce toxins like the major food contaminating mycotoxin aflatoxin (7).

Type III PKSs have the most simple domain structure functioning as single ketosynthase homodimers that use a variety of chain-type or aromatic acyl-CoA starter units and most commonly malonyl-CoA extender units for condensation reactions (8). The best studied members of this family belong to the chalcone synthases (CHSs) and stilbene synthases (STSs) representing hallmarks of plant secondary metabolism (4). Prominent examples of plant CHSs or STSs condense coumaroyl-CoA as a starter unit with three molecules of malonyl-CoA to naringenin chalcone or resveratrol, respectively (1).

Olivetol synthase (OLS) is a type III PKS that uses hexanoyl-CoA as a linear, short-chain acyl-CoA starter unit and three malonyl-CoA units to form an intermediate, which is further converted to olivetol (9). In the presence of the olivetolic acid cyclase (OAC), the tetraketide intermediate is cyclized to form olivetolic acid (OA), the precursor of $\Delta^9$-tetrahydrocannabinol in the cannabinoid biosynthetic pathway of *Cannabis sativa* (10). The use and recombinant expression of a type III PKS as a stand-alone olivetol synthase (OLS) to produce phytocannabinoids and therein coined as *Cannabis sativa* polyketide synthase/olivetol synthase enzyme (CsPKS/olivetol synthase) is disclosed in WO 2011/127589A1.

Phytocannabinoids, which are naturally produced in *Cannabis sativa*, other plants, and some fungi, have significant commercial value. Over 105 phytocannabinoids are known to be biosynthesized in *C. sativa*, or result from thermal or other decomposition from phytocannabinoids biosynthesized in *C. sativa*.

The taxonomic group of amoebozoa has revealed an unprecedented diversity of PKS genes with a hidden potential for natural products and novel biosynthetic pathways (11, 12). As an example, the model amoeba *Dictyostelium discoideum* harbors up to 45 potential PKS genes, whereby their enzymatic products have remained largely unknown (13, 14). Two genes encoding a natural genetic fusion of a type I fatty acid synthase and a type III PKS were first discovered and described in *D. discoideum* in 2006 and coined as PKS1 (StlA) and PKS37 (SUB) (FIG. 1A) (15) (see also US 2008-0233628A1 and US 2012-122180A1). The construction and recombinant expression of various synthetic fusion proteins of these two types of domains were claimed based on the existence of the two described natural examples from *D. discoideum*. The biological origin of the genes, synthetic examples, and the technical description of how to construct and express functional fusions in any specific biological host cells were not disclosed.

The gene lengths of approximately 10 kb, an A/T content of 75%, the presence of organism-specific introns and fundamental differences in the regulation of gene expression posed severe technical challenges to the expression of polyketide synthases, including natural hybrid PKSI-PKSIII hybrid genes from *D. discoideum* in a standard bacterial or fungal host cell, like *Escherichia coli* or *Saccharomyces cerevisiae*, respectively. Moreover, a functional synthetic hybrid enzyme and a product thereof has not been reported today.

WO 2018/148849A1 and US 2019-0367953A1 disclose the expression of sequence adapted Stl-proteins (therein named "DiPKS") in *S. cerevisiae* in order to produce polyketides in yeast. The polyketide synthase may be DiPKS and catalyzes the synthesis of olivetol or methyl-olivetol or a mixture thereof. The natural, wild-type DiPKS produces methyl-olivetol only. The DiPKS may be modified to produce olivetol only or a mixture of both olivetol and methyl-olivetol. However, both compounds are no precursors in the cannabinoid biosynthetic pathway and hence cannot be used for the production of THC.

Carvalho et al. (in: Carvalho, A.; Hansen, E. H.; Kayser, O.; Carlsen, S.; Stehle, F., Designing microorganisms for heterologous biosynthesis of cannabinoids. *FEMS Yeast Res* 2017, 17 (4), doi:10.1093/femsyr/fox037) review the potential use of synthetic biology as an alternative strategy for synthesis of cannabinoids in heterologous hosts, and summarize the knowledge surrounding cannabinoids biosynthesis and present a comprehensive description of the key steps of the genuine and artificial pathways, systems biotechnology needs, and platform optimization.

Tan et al. (in: Tan, Z.; Clomburg, J. M.; Gonzalez, R., Synthetic pathway for the production of olivetolic acid in *Escherichia coli*. *ACS Synth Biol* 2018, 7 (8), 1886-1896, doi: 10.1021/acssynbio.8b00075) disclose a synthetic approach to engineer *Escherichia coli* for the production of OA. Polyketide synthase and cyclase enzymes, OLS and OAC, were expressed with auxiliary enzymes aiming at increasing the supply of hexanoyl-CoA and malonyl-CoA as starting and extender units, respectively. The integration of additional auxiliary enzymes to increase hexanoyl-CoA and malonyl-CoA, along with evaluation of varying fermentation conditions enabled the synthesis of 80 mg/L OA.

Luo et al. (in: Luo, X.; Reiter, M. A.; d'Espaux, L. et al., Complete biosynthesis of cannabinoids and their unnatural analogues in yeast. *Nature* 2019, 567 (7746), 123-126, doi: 10.1038/s41586-019-0978-9) report the complete biosynthesis of the major cannabinoids cannabigerolic acid, $\Delta^9$-tetrahydrocannabinolic acid, cannabidiolic acid, $\Delta^9$-tetrahydrocannabivarinic acid and cannabidivarinic acid in *Saccharomyces cerevisiae*, from the simple sugar galactose. Overall, 16 genes were necessary in order to produce THC.

While the *C. sativa* plant is also a valuable source of grain, fiber, and other material, growing *C. sativa* for phytocannabinoid production, particularly indoors, is costly in terms of energy and labor, and the subsequent extraction, purification, and fractionation of phytocannabinoids from the *C. sativa* plant is also labor and energy intensive. It is therefore an object of the present invention to provide methods and means for the production of naturally-occurring phytocannabinoids by other means. Polyketides, including olivetolic acid and its analogues are valuable precursors for phytocannabinoids, such as the pharmacological most relevant phytocannabinoid THC. Other objects and advantages will become apparent to the person of skill when studying the present description of the present invention.

In a first aspect of the present invention, this object is solved by providing a gene encoding a hybrid protein of polyketide synthase 37 (PKS37) in which the C-terminal type III PKS domain or a functional fragment thereof is replaced by a plant olivetol synthase (OLS) or a functional fragment thereof, wherein said pks37 or functional fragment thereof is preferably derived from *Dictyostelium discoideum*. More preferably, the hybrid according to the present invention comprises amino acids 1 to 2618 of PKS37 from *D. discoideum*, and amino acids 2 to 385 of OLS from *C. sativa*. The gene sequence of the C-terminal OLS-part can be codon adapted for optimized expression in *D. discoideum*. OA was produced in cells of *D. discoideum* expressing this amoeba-plant-hybrid protein. Higher levels of OA were produced upon expression of olivetolic acid cyclase (OAC) in the same cells.

In a second aspect of the present invention, the above object is solved by providing a multi-gene expression vector for the recombinant production of olivetolic acid (OA) in a host species selected from amoebozoa, comprising and expressing the genes for medium-chain fatty acid CoA ligase (FadK), plant olivetol synthase (OLS), plant olivetolic acid cyclase (OAC), and Tobacco etch virus (TEV) peptidase or homologous genes thereof or functional fragments thereof, wherein said genes are transcribed as a single polycistronic mRNA spaced apart by viral 2A sequences. Preferably, said medium-chain fatty acid CoA ligase (FadK) is derived from *E. coli*, the plant olivetol synthase (OLS) and/or plant olivetolic acid cyclase (OAC) is derived from *C. sativa*.

In a third aspect of the present invention, the above object is solved by providing a multi-gene expression vector for the recombinant production of olivetolic acid (OA) in a host species selected from amoebozoa, comprising and expressing, the hybrid-gene according to the present invention, a plant olivetolic acid cyclase (OAC), and Tobacco etch virus (TEV) peptidase or homologous genes thereof or functional fragments thereof, wherein said genes are transcribed as a single polycistronic mRNA spaced apart by viral 2A sequences. Preferably, said plant olivetol synthase (OLS) and/or plant olivetolic acid cyclase (OAC) is derived from *C. sativa*.

In a fourth aspect of the present invention, the above object is solved by providing a recombinant amoebozoa host species, comprising and expressing the multi-gene expression vector according to the present invention, wherein said species is preferably selected from *Dictyostelium discoideum*.

In a fifth aspect of the present invention, the above object is solved by a method for the recombinant production of olivetolic acid (OA) in a species selected from amoebozoa, comprising the steps of a) culturing the recombinant amoebozoa species according to the present invention comprising and expressing the multi-gene expression vector according to the present invention in a suitable culture medium, wherein said culture medium is supplemented with hexanoic acid as precursor, and b) isolating said OA from said culture of step a).

In a sixth aspect of the present invention, the above object is solved by a method for the recombinant production of olivetolic acid (OA) in a species selected from amoebozoa, comprising the steps of a) culturing the recombinant amoebozoa species according to the present invention comprising and expressing the multi-gene expression vector according to the present invention in a suitable culture medium without the need of hexanoic acid supplementation, and b) isolating said OA from said culture of step a).

Another aspect of the present invention relates to the use of the hybrid-gene according the present invention, the multi-gene expression vector according to the present invention and/or the recombinant amoebozoa host species according to the present invention for the recombinant production of olivetolic acid (OA).

A further aspect of the present invention relates to the use of the hybrid-gene or protein according to the present invention, and/or recombinant bacteria, yeast or fungal host species for the recombinant production of olivetolic acid (OA).

Yet another aspect of the present invention relates to a method for producing $\Delta^9$-tetrahydrocannabinol and/or other cannabinoids, comprising the steps of performing the method according to the present invention, and converting the olivetolic acid (OA) as produced into $\Delta^9$-tetrahydrocannabinol or other cannabinoids.

As PKS37 represents a unique fusion enzyme of a fatty acid synthase (FAS) and a PKS III domain, the inventors assumed that the hexanoyl starter unit may also be handed over to another type III PKS upon fusion to the FAS enzymatic unit. Therefore, the inventors engineered an amoeba/plant PKS hybrid for the biosynthesis of OA exclusively from primary metabolic precursors and to determine the mechanistic function of the PKS37/FAS in the polyketide biosynthesis. This resulted in the first functional inter-kingdom hybrid that is able to conveniently produce the OA precursor 3,5,7-trioxododecanoyl-CoA using the hexanoyl-intermediate directly provided by the amoeba FAS. The intermediate was then further cyclized by OAC to produce the final polyketide product OA.

Therefore, the present invention provides a valuable tool for the synthesis of OA both in the form of a hybrid gene (nucleic acid) and protein (amino acid) of polyketide synthase 37 (PKS37) in which the C-terminal type III PKS domain or a functional fragment thereof in the protein is replaced by a plant olivetol synthase gene (OLS) or a functional fragment thereof. As shown here as proof of concept, in a preferred embodiment, the hybrid comprises amino acids 1 to 2618 of PKS37 from *Dictyostelium discoideum*, and amino acids 2 to 385 of OLS from *Cannabis sativa*. The present invention further provides the respective gene expression product, i.e. the hybrid-polypeptide of PKS37 or a functional fragment thereof with the C-terminal OLS or a functional fragment thereof. It was surprisingly found that the replacement of the type III PKS domain by OLS resulted in a functional polypeptide. Preferred is the hybrid or fusion of amino acids 1 to 2618 of PKS37 from *D. discoideum*, and amino acids 2 to 385 of OLS of *C. sativa*.

In the context of the present invention, the term "polyketide synthase 37 (PKS37)" when relating to the N-terminal part thereof, shall include all proteins that provides the hexanoyl-moiety to the C-terminal OLS thereof. Preferred is the N-terminal part ("PKS37/fatty acid synthase (FAS)") of the hybrid-gene or enzyme selected from *D. discoideum* and fused to the plant olivetol synthase (OLS) that is preferably selected from *C. sativa*.

In the context of the present invention, the term "olivetol synthase (OLS)" shall include all type III PKS domains that accept fatty acid moieties provided by a type I PKS domain or a fatty acid synthase domain. The olivetol synthase (OLS) is preferably selected from *C. sativa*.

In the context of the present invention, the term "functional fragment" or "functional variant" when referring to the polypeptides as mentioned herein or the genes encoding the same refers to a part, fragment or variant thereof which has the same biological function(s) as the polypeptide from which it has been derived. Such property comprises, for example, the enzymatic activity or activities. A "variant" is either a modified amino acid sequence that maintains or at least substantially maintains the biological function(s) as the polypeptide from which it has been derived. In the context of a nucleic acid ("gene") a variant comprises modified nucleotides that still encode for the nucleic acid encoding for the polypeptides as mentioned herein or the functional fragments or functional variants thereof. One example is a codon-optimized, e.g. for amoebozoa-, such as *Dictyostelium discoideum*-, codon-optimized nucleotide sequence (see, for example: Vervoort, E. B.; van Ravestein, A.; van Peij, N. N. et al., Optimizing heterologous expression in *Dictyostelium*: importance of 5' codon adaptation. Nucleic Acids Res 2000, 28 (10), 2069-74, doi:10.1093/nar/28.10.2069).

As preferred examples for enzymatic activity or activities, in the context of the present invention, the medium-chain fatty acid CoA ligase (FadK) acts as medium-chain fatty acid CoA ligase that can activate hexanoic acid to hexanoyl-CoA following its uptake as an externally provided precursor (21). Olivetol synthase (OLS) and olivetolic acid cyclase (OAC), condense the hexanoyl-CoA starter molecule with three internally provided malonyl-CoA units and cyclize the tetraketide to form OA, respectively. Tobacco etch virus (TEV) peptidase removes the viral 2A peptides from the separately translated proteins. In the PKS37/OLS hybrid protein, the N-terminal part ("PKS37/fatty acid synthase (FAS)") of the hybrid-gene or enzyme as herein provides the hexanoyl-moiety to the OLS for the condensation with three internally provided malonyl-CoA units to produce OA along with the OAC.

In the context of the present invention, the term "homologous" when referring to the polypeptides as mentioned herein or the nucleic acids encoding the same refers to related polypeptides or nucleic acids sharing a certain degree of identity and biological function(s) as the polypeptide from which they are derived. Preferred examples of homologous polypeptides or nucleic acids come from related species or belong to the same enzymatic class. Homologous polypeptides or nucleic acids share at least 50%, 60%, 70%, 80%, 90% 91%, 92%, 93%, 94%, 95%, 96%, 97%, 98% or 99% sequence identity with the polypeptides as mentioned herein or the nucleic acids encoding the same or the functional fragments thereof. As an example, see the disclosure with respect to the medium-chain fatty acid CoA ligase (FadK), below.

Another aspect of the present invention then relates to a multi-gene expression vector for the recombinant production of olivetolic acid (OA) in a host species selected from amoebozoa, comprising and expressing the genes for medium-chain fatty acid CoA ligase (FadK), plant olivetol synthase (OLS), plant olivetolic acid cyclase (OAC), and Tobacco etch virus (TEV) peptidase or homologous genes thereof or functional fragments thereof, wherein said genes are transcribed as a single polycistronic mRNA spaced apart by viral 2A sequences.

Preferred is the multi-gene expression vector according to the present invention, wherein said medium-chain fatty acid CoA ligase FadK is selected from FadK of *E. coli*, *Eggerthella lenta*, *Kosakonia radicincitans*, Enterobacteriaceae bacterium, *Dickeya zeae* ECJ, *Sutterella wadsworthensis*, *Clostridium clostridioforme*, *Citrobacter amalonaticus*, *Citrobacter braakii*, *Citrobacter werkmanii*, *Escherichia albertii*, *Actinobacteria bacterium*, *Citrobacter portucalensis*, *Yersinia massiliensis*, and *Serratia fonticola*.

Preferred is the multi-gene expression vector according to the present invention, wherein said plant olivetol synthase (OLS) is selected from *C. sativa*, a chalcone synthase of *Humulus lupulus*, *Morus notabilis*, *Jatropha curcas*, *Microcos paniculata*, and PKS III of *Trema orientale*. Preferred is the multi-gene expression vector according to the present invention, wherein said plant olivetolic acid cyclase (OAC) is selected from *C. sativa*.

In this aspect, the inventors designed a biosynthetic pathway for the production of OA built on the medium-chain fatty acid CoA ligase FadK (of *E. coli* (21)), and the enzymes olivetol synthase (OLS, *C. sativa*) and olivetolic acid cyclase (OAC, *C. sativa*) (9, 10). In order to express all required genes in the model strain *D. discoideum*, a multi-gene expression vector was established based on the previously reported pV2A-T system (22, 27). Transcription of the OA biosynthetic cluster yielded in a single polycistronic mRNA. Each gene was spaced by viral 2A sequences leading to the translation of separate proteins with the 2A peptides being removed by a co-expressed Tobacco etch virus (TEV) peptidase (FIG. 4B). HR-MS data of culture extracts from the transformed (pChR2) strain revealed heterologous OA biosynthesis following supplementation of hexanoic acid to the growth medium (FIG. 4D). These data show that *D. discoideum* can serve as an alternative chassis for the heterologous production of eukaryotic metabolites.

Another aspect of the present invention then relates to a multi-gene expression vector for the recombinant production of olivetolic acid (OA) in a host species selected from amoebozoa, comprising and expressing, the hybrid-gene according to the present invention as disclosed above, a plant olivetolic acid cyclase (OAC), and Tobacco etch virus (TEV) peptidase or homologous genes thereof or functional fragments thereof, wherein said genes are transcribed as a single polycistronic mRNA spaced apart by viral 2A sequences.

In this aspect, the inventors designed a biosynthetic pathway for the direct production of OA in *D. discoideum* from primary metabolic precursors. In order to express all required genes in the model strain *D. discoideum*, a multi-gene expression vector was established also based on the previously reported pV2A-T system (22, 27). Again, transcription of the hybrid, OAC and TEV genes yielded in a single polycistronic mRNA. Each gene was spaced by viral 2A sequences leading to the translation of separate proteins with the 2A peptides being removed by a co-expressed Tobacco etch virus (TEV) peptidase.

As mentioned above, functionally, the N-terminal part ("PKS37/fatty acid synthase (FAS)") of the hybrid-gene or enzyme produces a hexanoic acid-intermediate that is directly transferred from the pantetheine arm of the ACP domain to the catalytic cysteine residue of the adjacent plant type III PKS. Then, the OLS together with the OAC efficiently synthesize OA via three polyketide extensions of the hexanoyl precursor with malonyl-CoA and a final intramolecular C2 to C7 aldol condensation.

Preferred is the multi-gene expression vector according to the present invention, wherein the N-terminal part ("PKS37/fatty acid synthase (FAS)") of the hybrid-gene or enzyme is selected from *D. discoideum* and fused to the plant olivetol synthase (OLS) that is preferably selected from *C. sativa*. As for the other expression system according to the present invention, the plant olivetol synthase (OLS) fused to the C-terminus is preferably selected from *C. sativa*, a chalcone synthase of *Humulus lupulus, Morus notabilis, Jatropha curcas, Microcos paniculata*, and PKS III of *Trema* orientate. Further preferred is the multi-gene expression vector according to the present invention, wherein said plant olivetolic acid cyclase (OAC) is selected from *C. sativa*.

More preferred is the multi-gene expression vector or the hybrid-gene according to the present invention, wherein said plant olivetol synthase (OLS) and/or plant olivetolic acid cyclase (OAC) is derived from *C. sativa*.

It is also preferred for the multi-gene expression vector according to the present inventions that the genes are codon optimized for the expression in said amoebozoa host species, wherein said species is preferably selected from *Dictyostelium discoideum*. The *Dictyostelium* genome, for example, has a higher AT content than, for example, human or plants, resulting in a different codon preference. Optimizing codons can contribute to increased expression levels, maybe because of ribosome stabilization. Furthermore, adapting the 5'-sequence of the gene to the *Dictyostelium* 'Kozak'-like sequence may increase expression levels further, e.g. to a total of 6- to 8-fold increase in expression levels (see, for example: Vervoort, E. B.; van Ravestein, A.; van Peij, N. N. et al., Optimizing heterologous expression in *Dictyostelium*: importance of 5' codon adaptation. Nucleic Acids Res 2000, 28 (10), 2069-74, doi:10.1093/nar/28.10.2069). Methods for codon optimization are known in the art, and may comprise PCR amplification with a mutant oligonucleotide.

More preferred is the multi-gene expression vector according to the present invention, wherein said vector further comprises a suitable selection marker, such as, for example, selected from G418, blasticidin S, bleomycin, and hygromycin.

Another aspect of the present invention then relates to a recombinant amoebozoa host species, comprising and expressing the multi-gene expression vector and/or the hybrid-gene according to the present invention, wherein said species is preferably selected from *Dictyostelium discoideum*. Further useful amoebozoa species are, for example, *Dictyostelium mucoroides, Dictyostelium pupureum*, or *Polysphondylium*, such as *Polysphondylium pallidum*.

Another aspect of the present invention then relates to a method for the recombinant production of olivetolic acid (OA) in a species selected from amoebozoa, comprising the steps of a) culturing the recombinant amoebozoa species according to the present invention comprising and expressing the multi-gene expression vector according to the present invention in a suitable culture medium, wherein said culture medium is supplemented with hexanoic acid as precursor, and b) isolating said OA from said culture of step a).

As mentioned above, this method provides heterologous OA biosynthesis following supplementation of hexanoic acid to the growth medium. Conditions for culturing recombinant amoebozoa species, such as, for example *Dictyostelium discoideum*, are known from the literature, and comprise, for example, HL5 medium supplemented with 10 g/L glucose and 10 μg/mL G418.

Another aspect of the present invention then relates to a method for the recombinant production of olivetolic acid (OA) in a species selected from amoebozoa, comprising the steps of a) culturing the recombinant amoebozoa species according to the present invention comprising and expressing the multi-gene expression vector according to the present invention in a suitable culture medium without the need of hexanoic acid supplementation, and b) isolating said OA from said culture of step a).

As mentioned above, this method provides a biosynthetic pathway for the direct production of OA in the recombinant amoebozoa species, such as *D. discoideum*, from primary metabolic precursors.

Isolating the OA from the cultures can be achieved as disclosed in the examples herein and the respective literature. The cultures can be continuous and discontinuous, and be performed in large-scale fermenters.

The methods according to the present invention can further comprise a suitable induction of the expression, such as, for example by tetracycline or doxycycline and the respective inducible promotors, and/or comprise a suitable selection, such as, for example selected from G418, blasticidin S, bleomycin, and hygromycin.

Another aspect of the present invention then relates to a method for producing $\Delta^9$-tetrahydrocannabinol and/or other cannabinoids, comprising the steps of performing the method according to the present invention, and converting the olivetolic acid (OA) as produced into $\Delta^9$-tetrahydrocannabinol and/or other cannabinoids. This can be achieved, for example, by enzymatic condensation with the precursor geranyl phosphate, and subsequent conversion of cannabigerolic acid and/or derivatives thereof into tetrahydrocannabinolic acid and/or derivatives thereof.

Another aspect of the present invention then relates to the use of the hybrid-gene according to the present invention, the multi-gene expression vector according to the present invention and/or the recombinant amoebozoa host species according to the present invention for the recombinant production of olivetolic acid (OA) and for producing $\Delta^9$-tetrahydrocannabinol as disclosed herein and above.

Amongst other aspects thereof, the present invention shows that homologous and heterologous PKS genes can be functionally expressed in *D. discoideum* as a host for production and isolation of the corresponding polyketides directly from culture extracts of the amoeba. The developed platform enables the in vivo production of already known polyketides and to elucidate novel natural products of polyketide origin in amoeba. PCP production exceeded the one in native cells by orders of magnitude. The presence of numerous PKS genes and the relatively high levels of PCP in vegetative cells upon pks37 overexpression assume that *D. discoideum* provides a sufficient supply of various acyl- CoAs, primarily malonyl-CoA. It was thus shown that the amoeba can serve as a suitable, alternative expression host for any PKS that depends on these as starter and extender units.

Indeed, the stilbene cis-resveratrol was produced after heterologous expression of the corresponding plant PKS gene, and co-feeding of p-coumaric acid as precursor. Most approaches and studies of the heterologous production of such plant metabolites in addition required the implementation of further accessory pathways to secure the proper supply of coumaroyl-CoA (24-26). In *D. discoideum*, this may be well accomplished by a native p-coumaroyl-CoA ligase encoded by three nearly identical, neighboring gene copies (11). This suggested that the amoeba can also serve as suitable expression chassis for exogenous PKSs that use the same starter units.

OA is synthesized from hexanoyl starter molecules and also shares the malonyl-CoA derived resorcinol moiety with PCP. Upon expression of the OLS and OAC from *C. sativa*, along with the bacterial fadK to activate hexanoic acid, feeding of the precursor resulted in the production of OA. Notably, the side product olivetol, that would be produced by OLS in the absence of OAC (10), was not detected by MS measurements.

This indicates an advantageous complete polycistronic expression of the entire biosynthetic pathway and that the developed multi-gene expression system, which had originally been established only for filamentous fungi (27), can be successfully adapted to function in other eukaryotes.

As PKS37 represents a unique fusion enzyme of a fatty acid synthase (FAS) and a PKS III domain, the inventors assumed that the hexanoyl starter unit may also be handed over to another type III PKS upon fusion to the FAS enzymatic unit. To address this, the inventors engineered an amoeba/plant PKS hybrid for the biosynthesis of OA exclusively from primary metabolic precursors and to determine the mechanistic function of the PKS37/FAS in the polyketide biosynthesis. This resulted in the first functional inter-kingdom hybrid that is able to produce the OA precursor 3,5,7-trioxododecanoyl-CoA using the hexanoyl-intermediate directly provided by the amoeba FAS. The intermediate was then further cyclized by OAC to produce the final polyketide product OA. This was further proved by the loss-of-function mutant having a single serine to alanine substitution in the phosphopantetheine-binding site of the ACP domain. Thereby, the posttranslational activation of FAS by the phosphopantetheinyl transferase is prevented and results in an inactive apo-enzyme (28). The absence of OA in this mutant indicates that the hexanoyl precursor is provided by the PKS37/FAS domain and is not produced by the amoeba itself. However, it cannot be fully excluded that the FAS domain produces free hexanoyl-CoA that can subsequently be used by the OLS. However, this scenario could also apply to the native PKS37 and is rather unlikely, since the FAS part lacks a thioesterase domain, which is needed for releasing the acyl-CoA esters. Therefore, it can be assumed that the amoeba FAS produces a hexanoyl-intermediate that is directly transferred from the pantetheine arm of the ACP domain to the catalytic cysteine residue of the adjacent plant type III PKS; then, the OLS together with the OAC efficiently synthesize OA via three polyketide extensions of the hexanoyl precursor and a final intramolecular C2 to C7 aldol condensation.

Taken together, the inventors established the first synthetic inter-kingdom hybrid enzyme that enables OA biosynthesis from acetyl- and malonyl-CoA. The in vivo studies confirmed the proposed PCP biosynthesis and proved the mechanistic function of the FAS-like domain to produce the hexanoyl-intermediate. The data show the suitability of *D. discoideum* as expression host for analyzing combinatorial biosyntheses and opens new ways for the heterologous production of polyketide-derived natural products. In addition to its wide use as a model organism for studying cellular and developmental processes (29), the inventors have demonstrated here that the amoeba can be also used as an alternative chassis for the heterologous expression of eukaryotic metabolites.

The present invention will now be described further in the following examples with reference to the accompanying Figures, nevertheless, without being limited thereto. For the purposes of the present invention, all references as cited herein are incorporated by reference in their entireties.

FIG. 1 shows the PCP production by overexpression of pks37 in *D. discoideum*. (A) Schematic representation of the PKS37 FAS I-PKS III hybrid and structure of its proposed PKS product PCP. The N-terminal type I FAS and C-terminal type III PKS domains as well as their involvement in the PCP biosynthesis are indicated in gray and dark gray, respectively. The FAS contains a ketosynthase (KS), acyl-transferase (AT), dehydratase (DH), enoyl reductase (ER), ketoreductase (KR) and an acyl-carrier protein (ACP) domain as depicted. (B) Western blot analysis of total proteins extracted from *D. discoideum* wild-type and pks37-GFP strain. The pks37 gene was tagged with GFP at the C-terminus and expressed under control of the constitutive actin15 promoter. For the mutant strain, a specific band corresponding to PKS37-GFP (MW: 359.2 kDa) was detected using an anti-GFP antibody. (C) Northern blot analysis of total RNA isolated from the wild-type and pks37-oex strain. Hybridization was performed using a pks37-specific DNA probe. Transcription of pks37 was only detectable in the mutant strain. The amount of rRNA served as a loading control. (D) HPLC analysis of culture extracts from *D. discoideum* wild-type and pks37-oex mutants. While the GFP-tagged version shows no product formation, the untagged pks37 strain reveals the production of a compound eluting at 18.2 min. DAD chromatograms were extracted at λ=280 nm. Subsequent HR-MS analysis confirmed the presence of a compound with the m/z of 223.0965 [M−H]⁻ that correlates with the calculated mass of PCP. (E) Biosynthetic pathway of DIF-1. PCP is converted to DIF-1 by chlorination and O-methylation during the development of *D. discoideum*. (F) Metabolic analysis of *D. discoideum* fruiting bodies. After 26 h of development, wild-type and mutant fruiting bodies were harvested and analyzed for metabolite production. HR-MS data indicate the presence of all halogenated DIF-1 intermediates in the wild-type (black) and the pks37-oex strain (dark gray). Extracted ion chromatograms are shown for the calculated masses of PCP (m/z 223.0976 [M−H]⁻ (1)), Chloro-PCP (m/z 257.0586 [M−H]⁻ (2)), Dichloro-PCP (m/z 291.0196 [M−H]⁻ (3)) and DIF-1 (m/z 305.0353 [M−H]⁻ (4)).

Figure 2:
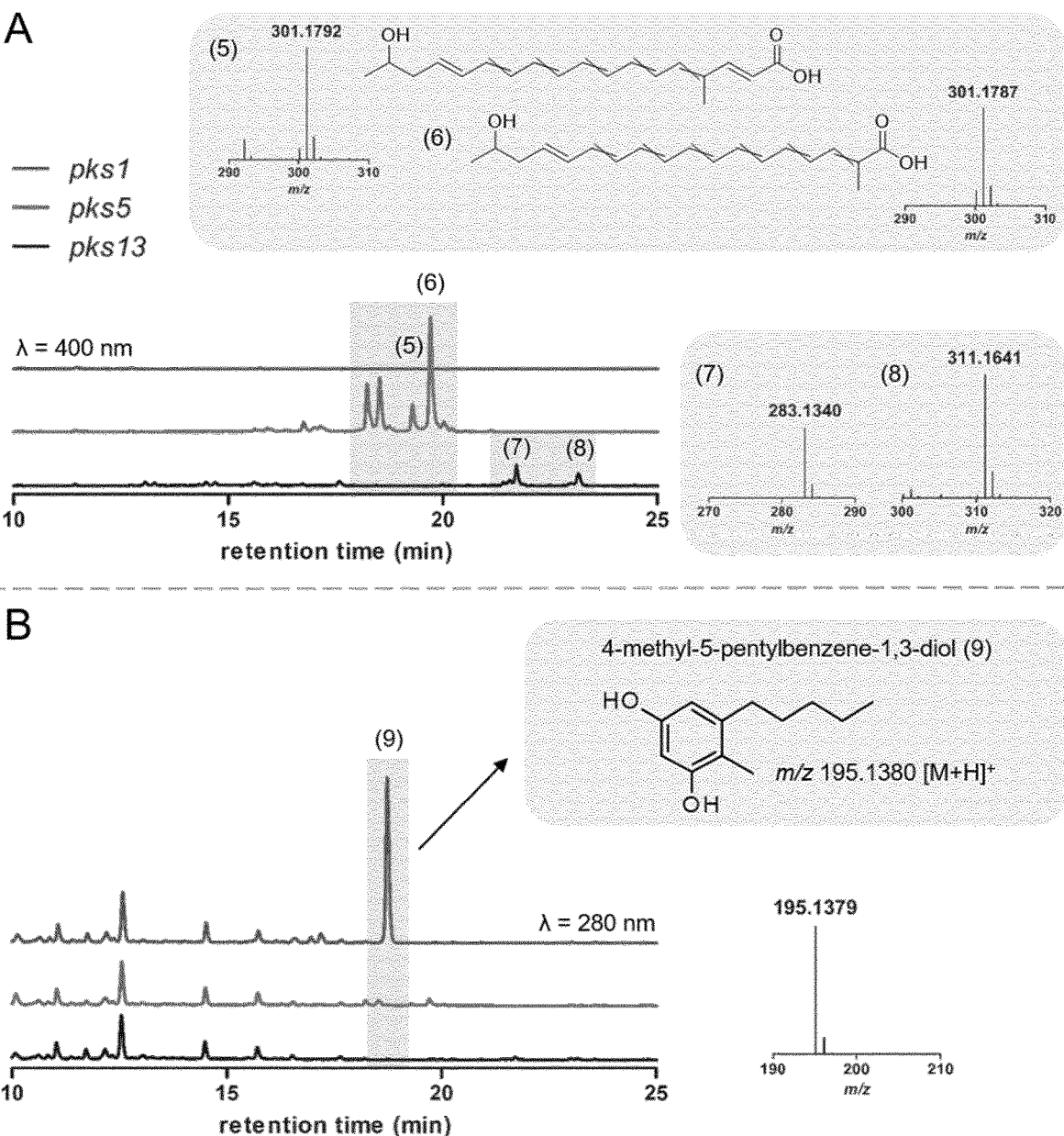

FIG. 2 shows the secondary metabolite production by amoeba PKSs. The pks1, 5 and 13 genes were overexpressed under control of the constitutively active actin15 promoter for three days and analyzed for metabolite production in *D. discoideum*. (A) DAD chromatograms extracted at λ=400 nm showed the presence of new metabolites for the pks5 (5,6) and pks13 (7,8) strains. Peak purification and subsequent HR-MS analysis disclosed the indicated mass spectra. For compounds isolated from the pks5-oex mutant, the corresponding chemical structures were elucidated by NMR as depicted. (B) DAD chromatograms extracted at λ=280 nm revealed a main peak for the pks1-oex strain with the m/z of 195.1379 $[M+H]^+$, confirming the 4-methyl-5-pentylben-zene-1,3-diol (9) as the main polyketide product in vivo.

Figure 3:
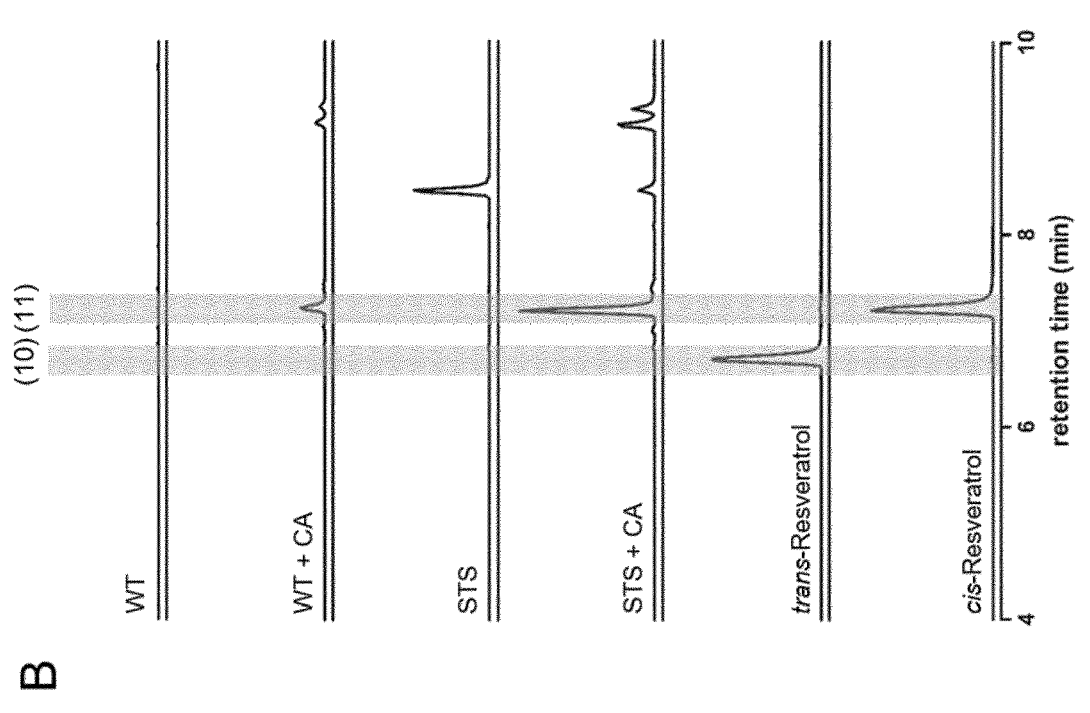

FIG. 3 shows the resveratrol production by heterologous expression of a plant type III PKS in *D. discoideum*. (A) Structural similarity of PCP with plant polyketides. PKS37 from *D. discoideum* contains a PKS III domain, which is similar to plant chalcone synthases (CHSs) or stilbene synthases (STSs) that condense coumaroyl-CoA and malo-nyl-CoA units to produce naringenin chalcone or resveratrol, respectively. (B) Metabolic analysis of culture extracts from *D. discoideum* wild-type and the STS-oex strain. After supplementation with 1 mM p-coumaric acid (CA) as pre-cursor, HR-MS data indicate the production of the plant polyketide cis-resveratrol in amoeba, without co-expression of a coumaroyl-CoA ligase (4CL) encoding gene. Extracted ion chromatograms are shown for the calculated mass of resveratrol (m/z 227.0714 $[M–H]^−$).

Figure 4:
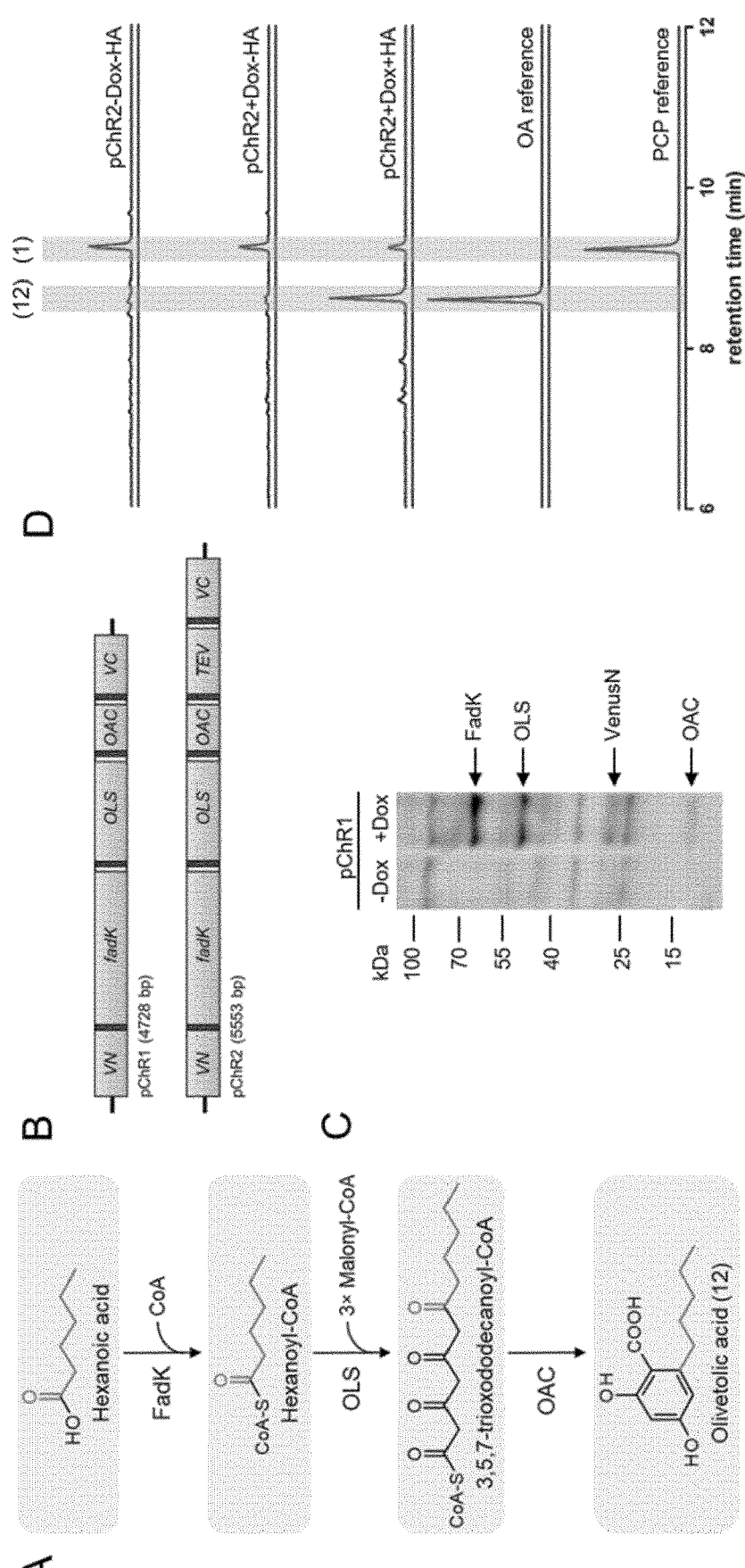

FIG. 4 shows the heterologous production of olivetolic acid in *D. discoideum*. (A) Designed synthetic pathway for the heterologous production of olivetolic acid (OA) by employing the acyl-CoA synthetase FadK from *E. coli*, and the *C. sativa* enzymes olivetol synthase (OLS) and olivetolic acid cyclase (OAC). (B) For expression studies, the fadK, OLS and OAC genes, along with the Venus subunits (VN and VC), were assembled and expressed under control of the inducible Tet$^{ON}$ promoter (pChR1). For metabolic analysis, the TEV sequence was additionally included (pChR2). Sequences encoding the 2A peptides and TEV cleavage sites are indicated in dark gray and gray, respectively. (C) Western blot analysis of total proteins extracted from the *D. discoi-deum* pChR1 strain grown under non-inducing (–Dox) and inducing (+Dox) conditions. Due to the missing TEV endo-peptidase, the 2A peptides at the C-terminus of the indicated proteins are not removed in vivo and can be detected by an anti-2A antibody. Proteins extracted from the induced strain show four specific bands corresponding to FadK (MW: ~66.1 kDa), OLS (MW: ~45.9 kDa), OAC (MW: ~15.3 kDa) and the VenusN subunit (MW: ~31 kDa). (D) HR-MS analysis of culture extracts from the pChR2 strain. Shown are the extracted ion chromatograms for the calculated mass of OA (m/z 223.0976 $[M–H]^−$). The mutant uninduced (–Dox) and induced (+Dox) without the addition of hexanoic acid (HA) shows no production of OA. Only by supplying the induced amoeba culture with 1 mM HA as precursor, a peak is detectable at the retention time of 8.65 min. The presence of OA and PCP was verified by direct comparison with the pure compounds as reference.

Figure 5:
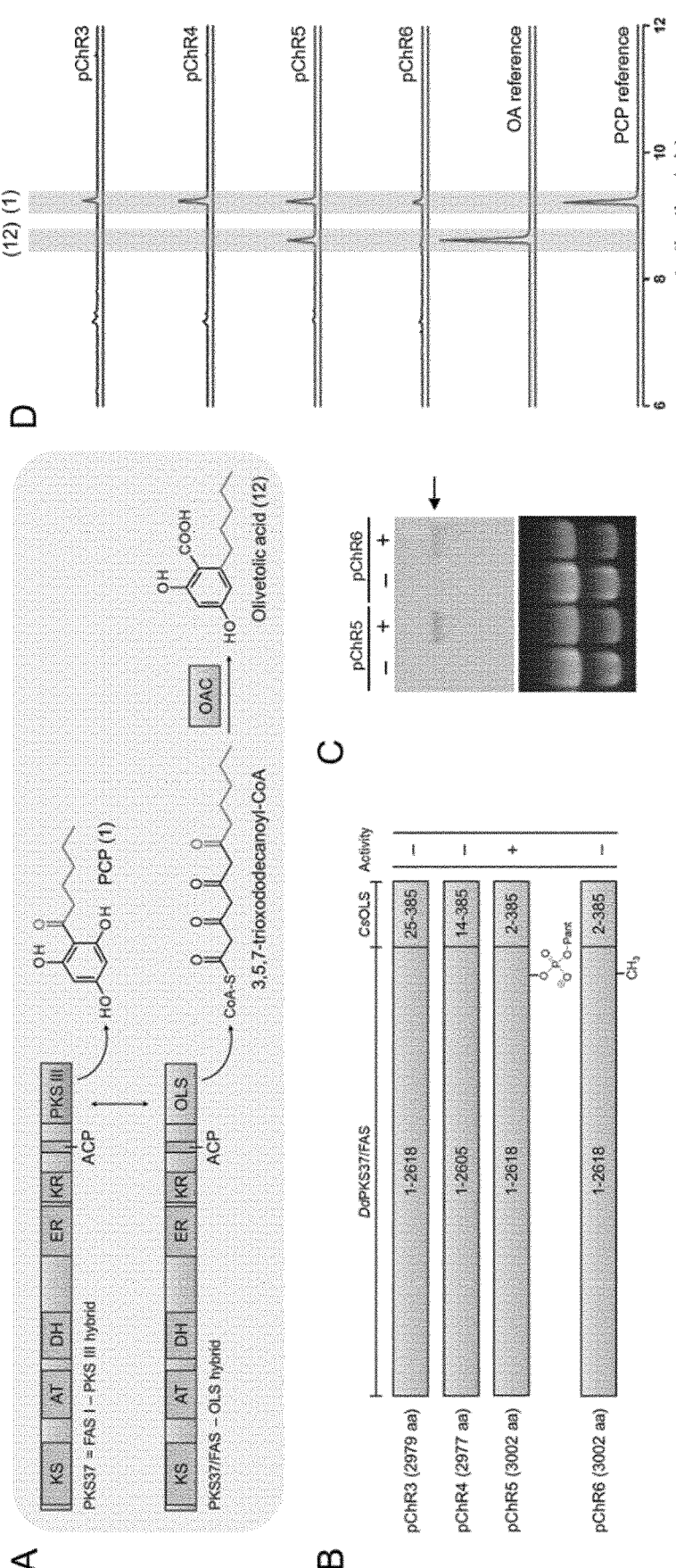

FIG. 5 shows the construction of a functional inter-kingdom PKS hybrid for OA biosynthesis. (A) Schematic representation of the PKS37/FAS-OLS hybrid for biosyn-thesis of OA in *D. discoideum*. The PKS37/FAS domain produces a hexanoyl-intermediate (light gray), which is used as starter unit by PKS III for the PCP biosynthesis. By swapping the PKS37/PKS III domain with the OLS of *C. sativa*, the amoeba FAS domain can provide the hexanoyl-moiety for the OA production by OLS and OAC. (B) Three different domain swapping constructs were generated as indicated (pChR3-5). As proof of the functional involvement of PKS37/FAS in the OA biosynthesis, a loss-of-function mutant of the pChR5 strain was generated by S2458A substitution in the phosphopantetheine-binding site of the FAS-ACP domain (pChR6). (C) Northern blot analysis of total RNA isolated from the pChR5 hybrid and its loss-of-function mutant pChR6. Hybridization was performed using a pks37-specific DNA probe. Both strains show transcription only after induction with doxycycline (+). Bands of rRNA are shown as a loading control. (D) HR-MS analysis of the pChR3-6 hybrid strains. Shown are the extracted ion chro-matograms for the calculated mass of OA (m/z 223.0976 $[M–H]$). HR-MS data revealed that only hybrid pChR5 shows production of OA. The absence of OA in the loss-of-function mutant pChR6 indicates that the hexanoyl pre-cursor is provided by the PKS37/FAS domain. The identity of OA and PCP was verified by direct comparison with pure reference compounds.

Figure 6:
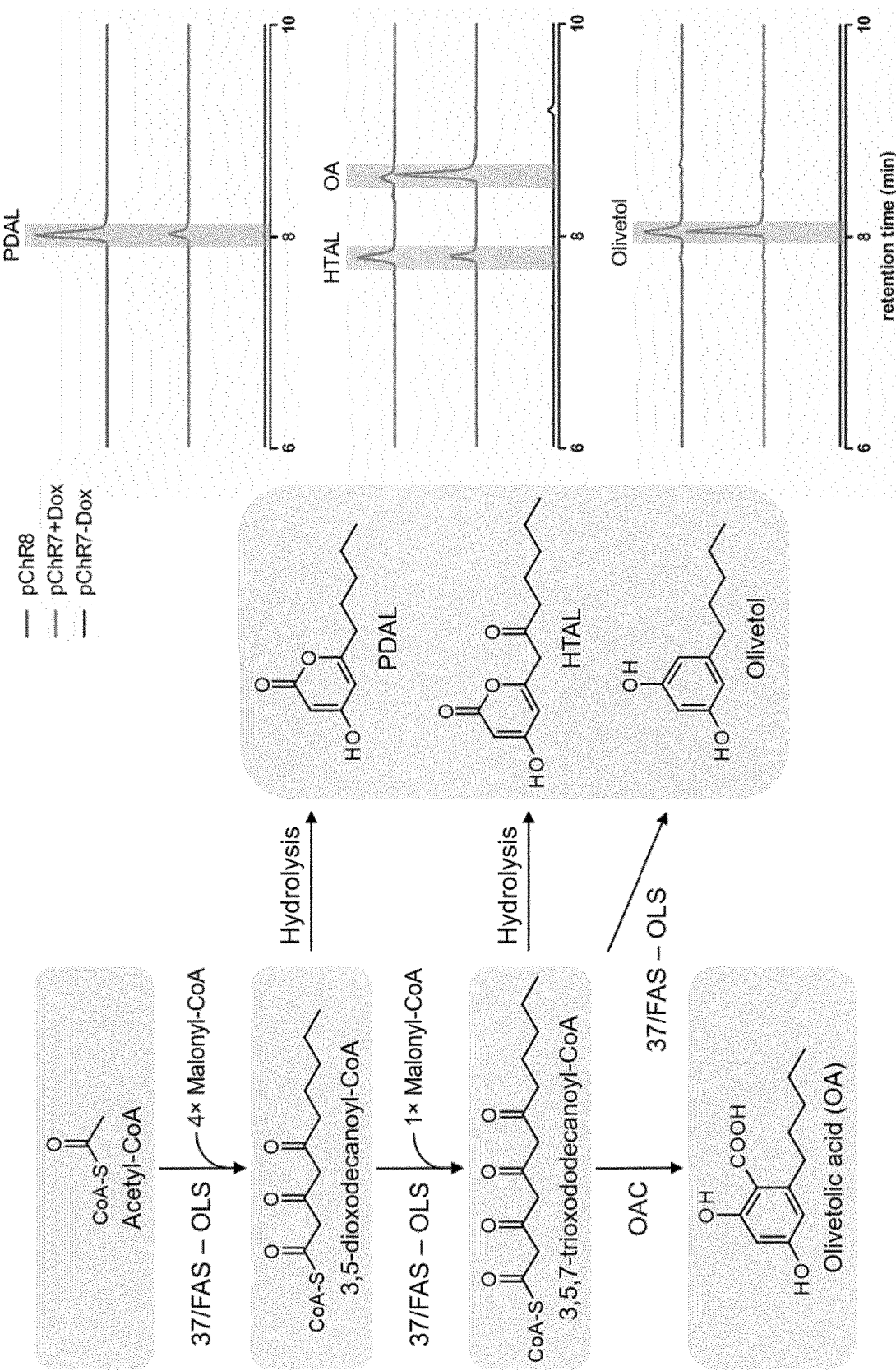

FIG. 6 shows the metabolic analysis of shunt product formation of the pChR7 and pChR8 strains. Depicted is the proposed biosynthetic pathway of olivetolic acid (OA) using the PKS37/FAS-OLS hybrid enzyme and the olivetolic acid cyclase (OAC). In absence of the OAC, the PKS37/FAS-OLS enzyme is proposed to produce olivetol and two α-pyrones, namely pentyl diacetic acid lactone (PDAL) and hexanoyl triacetic acid lactone (HTAL) as catalytic by-products. The hybrid was either expressed under control of the constitutively active actin15 promoter (pChR8 strain), or co-expressed with the OAC as a polycistron using the inducible Tet$^{ON}$ system (pChR7 strain). HR-MS data indi-cate the presence of all shunt products in both strains, whereby a higher abundance of α-pyrones is detectable in the pChR8 strain. Although traces of OA can also be observed in the pChR8 strain, the induced pChR7 strain (+Dox) shows a clear shift of the chemical equilibrium from α-pyrones towards OA formation. Shown are the extracted ion chromatograms for the calculated mass of PDAL (m/z 181.0870 $[M–H]$), HTAL (m/z 223.0976 $[M–H]$), Olivetol (m/z 179.1077 $[M–H]$) and OA (m/z 223.0976 $[M–H]^−$).

Figure 7:
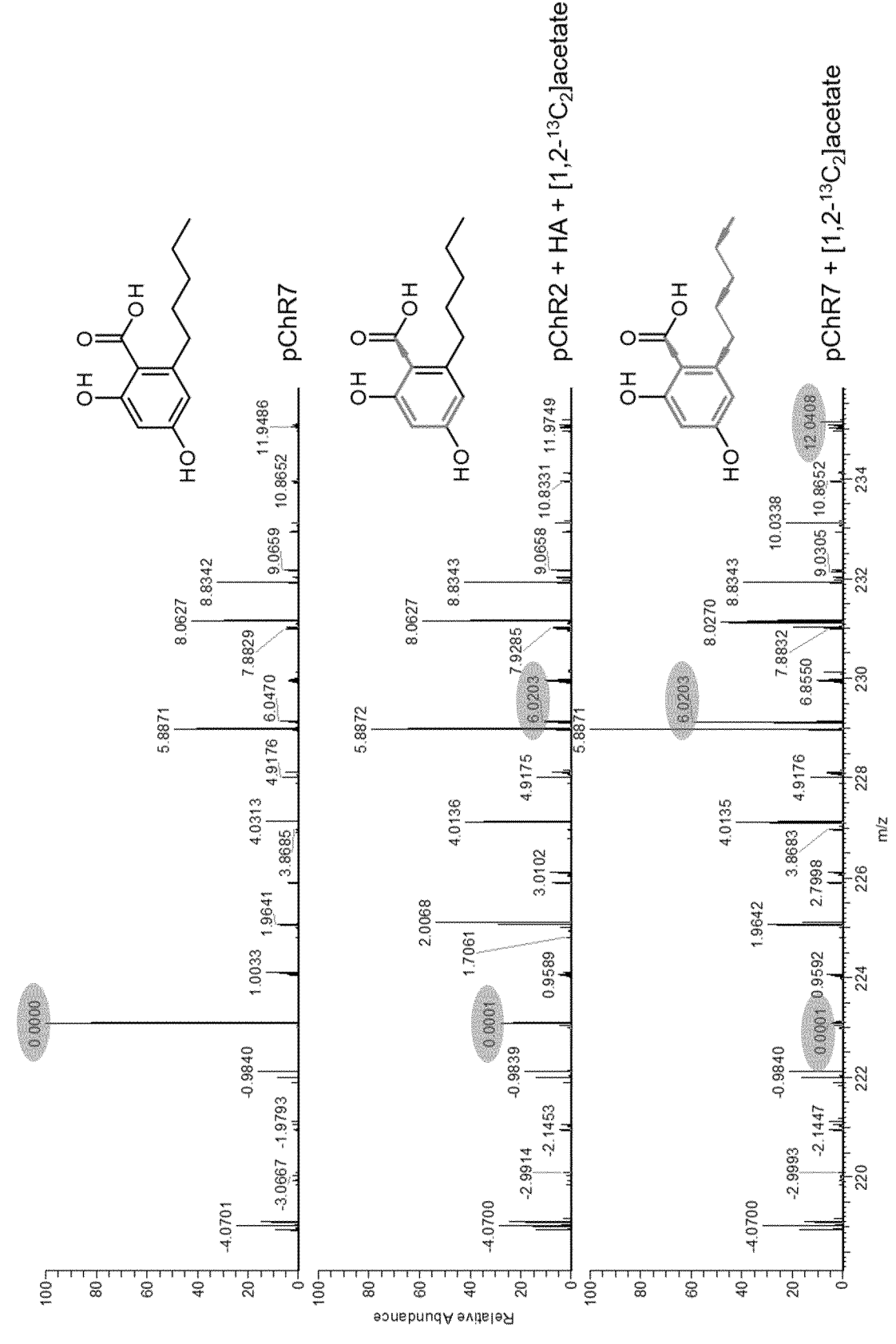

FIG. 7 shows HR-MS measurements of feeding experi-ments with isotopically-labeled acetate. The PKS37/FAS-OLS interkingdom hybrid (pChR7) and the fadK-containing pChR2 strain were grown in medium enriched with [1,2-$^{13}C_2$]acetate and analyzed by HR-MS. Feeding of the pChR2 strain with hexanoic acid (HA) and labeled acetate resulted in the incorporation of only three acetate-derived $C_2$ units into OA, while the HR-MS analysis of the pChR7 hybrid, supplemented with labeled acetate, shows a pattern as expected for a completely acetate-derived polyketide. Separate growth experiments were performed without the addition of the labeled precursor.

Figure 8:
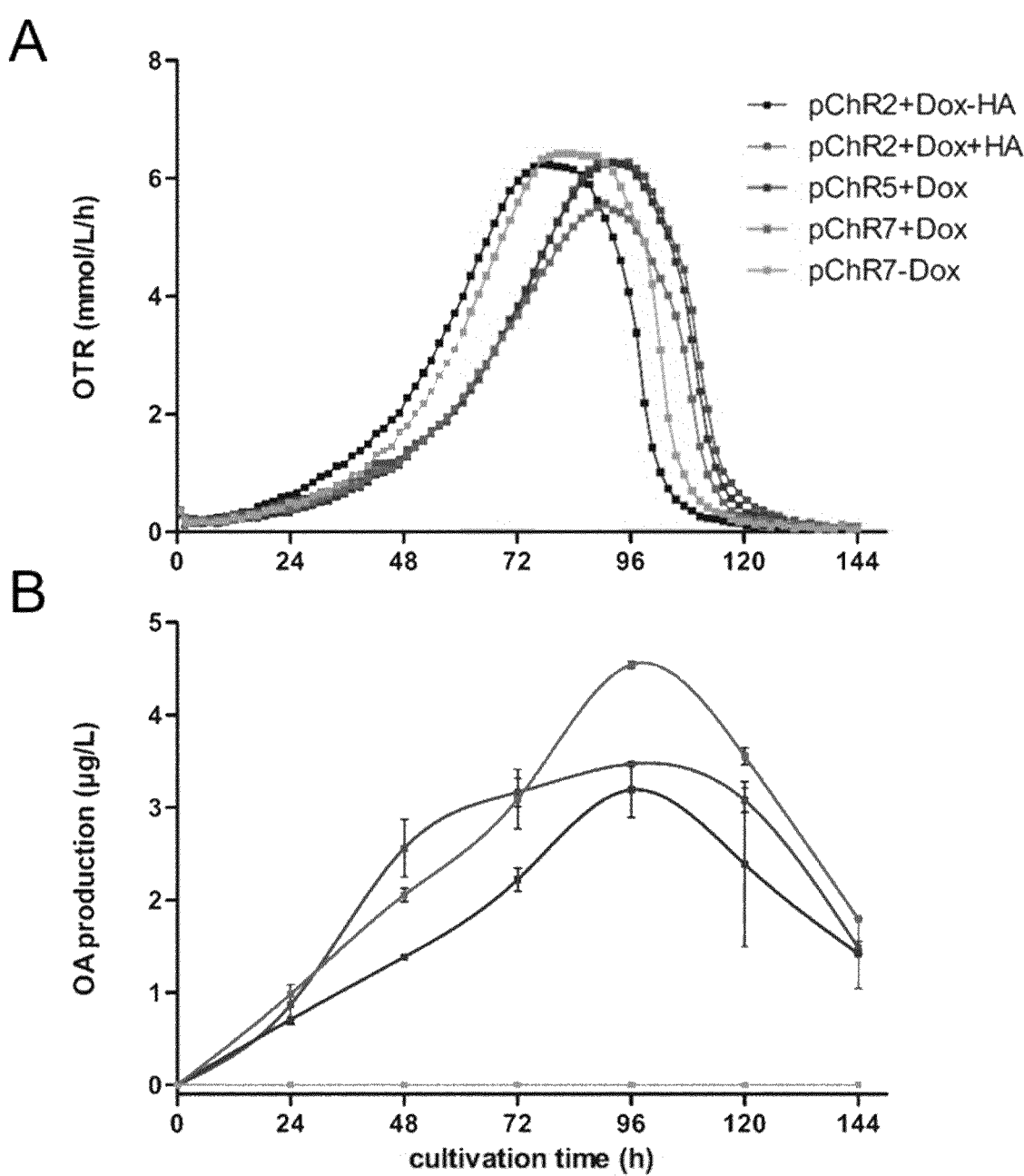

FIG. 8 shows the growth and metabolic activities of OA production strains. (A) Respiratory activity monitoring of the pChR5 hybrid, the codon-optimized pChR7 hybrid, and the fadK-based pChR2 strain grown in the presence (+HA) or absence of hexanoic acid (–HA), under non-inducing (–Dox) or inducing (+Dox) conditions as indicated. The oxygen transfer rate (OTR) shows the effect of heterologous pathway expression and hexanoic acid supplementation on the metabolic activity of the indicated strains. For clarity, only every fifth measuring point is represented by a symbol. (B) Production of OA from glucose or HA supplementation by strains indicated in (A). OA titers were determined by peak integration upon HR-MS analysis using an external OA reference, and reached a maximum after 96 h for all pro-ducing strains. Data represent mean values from two bio-logical replicates. Error bars: ±SEM.

EXAMPLES

Materials and Methods

*Dictyostelium* strains and cultivation. *Dictyostelium dis-coideum* AX2 cells were grown in HL5 complex medium (Formedium) supplemented with 1% [w/v] glucose at 22° C. in cell culture dishes or shake flasks at 140 rpm. Selection of recombinant amoebae was performed by adding 10

μg/mL G418 (InvivoGen) unless otherwise stated. For induction of the Tet$^{ON}$ polycistronic genes, amoeba cultures were supplied with 20 μg/mL doxycycline (AppliChem). For exogenous supply of precursors, cultures were supplemented with 1 mM p-coumaric acid (Merck) or 1 mM hexanoic acid (Merck) as indicated.

Construction of single-gene overexpression plasmids. Since the complete amplification of the full-length pks37 gene (Gene ID: 8627855) from genomic DNA did not yield in any product, the gene was amplified in two overlapping fragments and assembled into the pSK-GFP-srbA (30) as a cloning vector using seamless cloning. Oligonucleotides were obtained from Eurofins Genomics and are listed in Table 1. PCR amplifications were performed using the Phusion Flash High-Fidelity PCR Master Mix (Thermo Fisher). For expression analysis of pks37 in amoeba, the full-length gene was amplified from the cloning vector using primers [1]/[2] and introduced into the pTX vector in frame with a C-terminal GFP-tag (31, 32), under control of a constitutive actin15 promoter. For this purpose, the pTX-GFP vector was amplified by PCR using primer pair [3]/[4]. After DpnI digest of the template plasmid, PCR fragments were purified by gel extraction (GeneJET Gel Extraction Kit, Thermo Fisher) and assembled using the GeneArt Seamless Cloning & Assembly Kit (Thermo Fisher) according to the manufacturer's instructions. Recombinant plasmids were isolated from *E. coli* DH5α (GeneJET Plasmid Miniprep Kit, Thermo Fisher) and correct vector assemblies were verified by PCR and Sanger sequencing (LGC Genomics). A tag-free construct was generated as described above using primer pair [1]/[5] for amplification of pks37 and pair [6]/[7] for pTX vector linearization. In addition, the pTX vector was amplified using primers [8]/[4] and combined with pks1 (Gene ID: 8616850), pks5 (Gene ID: 8618014) and pks13 (Gene ID: 8618586) genes that were PCR-amplified using primer pair [9]/[10], [11]/[12] and [13]/[14], respectively. For resveratrol production, the pTX vector was linearized by PCR using primers [15]/[16] and assembled with the *V. vinifera* STS gene (Gene ID: 100256566) that was amplified using primer pair [17]/[18].

Generation of polycistronic multi-gene expression plasmids. For olivetolic acid production in amoeba, the genes of interest were provided with homologous tail regions for direct integration into the EcoRV-linearized pV2A-T vector (22). The fadK gene (Gene ID: 946213) was amplified from genomic DNA of *E. coli* K12 MG1655 using primers [19] and [20]. The genes for OLS (GenBank: AB164375.1) and OAC (JN679224.1) from *C. sativa* were synthesized by Eurofins Genomics and amplified using primer pair [21]/[22] and [23]/[24], respectively. The generated fragments were gel-purified and separately assembled into the pV2A-T vector by seamless cloning. According to the selected order, each plasmid was restricted either with SwaI (acceptor plasmid) or with PmeI (donor plasmid) for a stepwise combination of genes as reported (22). The final pV2A-T vector containing fadK, OLS, OAC and TEV (named as pV2A-T_OA) served as donor of the desired genes and was combined with a modified pDM310 vector that contains an inducible Tet$^{ON}$ promoter for expression in amoeba (33). For this purpose, the Venus-TEV cassette was amplified from the pV2A-T_TEV plasmid using primers [25]/[26] that contain an integrated Kozak-sequence and homologous regions for direct insertion into the BglII-linearized pDM310 vector (33). The resulting pDM310_Venus-TEV plasmid served as acceptor, which was subsequently digested with ZraI/AleI and combined with the PacI/SwaI-restricted pV2A-T_OA donor vector to create the final expression vector pChR2.

Correct assembly was verified by sequencing. To generate the pChR1 control vector, the pDM310 Venus-TEV plasmid was linearized by PCR using primer pair [27]/[28] and assembled with the PacI/SwaI-restricted pV2A-T_fadK-OLS-OAC plasmid.

To create the domain swapping constructs, the pChR2 vector backbone was amplified by PCR using primers [29] and [30] with an integrated XbaI recognition site between the 2A-tag and fadK to remove the generated linker region. After DpnI/XbaI digest, the vector backbone was gel-purified and combined with three different versions of the PKS37/FAS (A: 1-2618 aa, B: 1-2618 aa, C: 1-2605 aa) and OLS (A: 25-385 aa, B: 2-385 aa, C: 14-385 aa) fragments that were amplified using primer pair [31]/[32], [31]/[33], [31]/[34], [35]/[38], [36]/[38] and [37]/[38], respectively. The obtained plasmids (version A,B,C) are referred to as pChR3, pChR5 and pChR4, respectively. To generate the loss-of-function plasmid pChR6, a S2458A substitution was introduced into the PP-binding site of PKS37/FAS by pChR5 vector amplification using overlapping primers [39]/[40] that contain the corresponding nucleotide exchange. A new NsiI recognition site was introduced to screen for positive mutants and the correct mutagenesis was verified by sequencing. The functional pChR5 hybrid vector was further used as template for replacing the OLS and OAC genes with their codon-optimized version for *D. discoideum*. Codon optimization was performed based on the Kazusa Codon Usage Database using the GENEius software designed by Eurofins Genomics. The OLS-DD and OAC-DD optimized genes were synthesized from GenScript Biotech and Eurofins Genomics, respectively. The pChR5 vector backbone, and the synthetic OLS-DD and OAC-DD genes were amplified using primer pair [41]/[42], [43]/[44] and [45]/[46], respectively, and combined by seamless cloning to yield plasmid pChR7. In addition, the OLS-DD gene was PCR-amplified using primers [43]/[47] and used to replace the PKS III sequence of the pTX_pks37 plasmid that was amplified using primers [48]/[42], resulting in the pChR8 plasmid.

Transfection of amoeba by electroporation. Transfection of *D. discoideum* was performed as previously described (34) with some modifications. Briefly, *Dictyostelium* cells were harvested from mid-log phase by centrifugation for 5 min at 500×g and 4° C. The cells were washed in ice-cold electroporation buffer and re-suspended at a concentration of 4×10$^7$ cells/mL, determined using the CASY cell counter (Roche). Then, 1-5 μg of plasmid DNA were added to 100 μL of cell suspension in a pre-chilled 1 mm gap electroporation cuvette (BTX) and incubated for 5 min on ice. Electroporation was performed at 850 V, 25 μF and 25Ω using the ECM 630 cell electroporator (BTX). After pulsing, the cell suspension was mixed with 500 μL of HL5 medium containing 1% glucose and incubated for 4 h at 22° C. and 400 rpm. Then, the cells were dispensed on tissue culture plates containing HL5 medium supplemented with 1% glucose and 10 μg/mL G418 for selection of drug-resistant amoeba. Recombinant amoeba cells were sub-cultured at least two times before preparing permanent frozen stocks.

Western blot analysis. For Western blotting of the wild-type (as negative control) and the pks37-GFP strain, 1×10$^7$ cells of overnight cultures were pelleted by centrifugation for 5 min at 800×g and 4° C., and re-suspended into 150 μL lysis buffer (100 mM Tris/HCl, 1% SDS, 8 M Urea). The cell lysates were mixed with 6×SDS sample buffer and denatured for 10 min at 98° C. and 700 rpm. The extracted proteins were separated on Bolt™ 4-12% Bis-Tris Plus Gels (Thermo Fisher) and the corresponding 1× Bolt™ MOPS SDS Running Buffer (Thermo Fisher) for 40 min at 140 V. After separation by SDS-PAGE, the proteins were transferred to a 0.2 μm nitrocellulose membrane for 1 h at 25 V using the Mini Gel Electrophoresis Tank (Thermo Fisher). The membrane was blocked with TBS-T (20 mM Tris, 150 mM NaCl, 0.1% Tween 20) containing 3% BSA, and incubated overnight at 4° C. with mild shaking. For detection, an anti-GFP antibody (GF28R, Thermo Fisher) was used in combination with a goat anti-mouse IgG-AP antibody (Santa Cruz). The membrane was washed in assay buffer (20 mM Tris, 1 mM $MgCl_2$, pH 9.8), developed by adding CDP-Star solution (Applied Biosystems) and imaged using the FUSION FX imaging system (Vilber Lourmat). For Western blot analysis of the 2A-tagged proteins, the *D. discoideum* pChR1 strain was grown under non-inducing conditions (as negative control) or in the presence of 20 μg/mL doxycycline. Cell harvesting and sample preparation was performed as described above. The 2A-tagged proteins were separated on Novex™ 8-16% Tris-Glycine Gels (Thermo Fisher) and blotted onto a PVDF membrane. For detection, an anti-2A antibody (ABS31, Merck) was used in combination with a goat anti-rabbit IgG-AP antibody (A3687, Merck).

Northern Hybridizations. RNA was isolated from $5 \times 10^7$ amoeba cells using the RNeasy Mini Kit (QIAGEN). For each sample, 20 μg of total RNA were separated on a 1.2% denaturing agarose gel containing 2% formaldehyde in MOPS buffer. The gel was washed in 0.25 M HCl solution, denaturation solution (10 g NaOH, 44 g NaCl, 500 mL) and 10×SSC solution (87.7 g NaCl, 44.1 g sodium citrate, 500 mL), and blotted overnight on a Nylon membrane. After UV-crosslinking, the membrane was pre-hybridized at 48° C. for 5 h in hybridization buffer (5×SSC, 1% SDS, 0.1% N-laurylsarcosyl, 5 M Urea, 50 mM sodium phosphate, pH 7.0) containing 5% Roche blocking solution. Hybridization was performed overnight at 60° C. using a pks37-specific Digoxigenin (DIG)-labeled DNA probe that was constructed by amplification from genomic DNA using the DreamTaq Green PCR Master Mix (Thermo Fisher), DIG-ddUTPs (Jena Bioscience) and primers [49]/[50]. The membrane was washed, blocked with maleic acid buffer (0.1 M maleic acid, 0.1 M NaCl, pH 7.5) containing 10% Roche blocking reagent and incubated with an Anti-DIG AP-conjugated antibody (Roche). The blot was equilibrated in detection buffer and developed as described above.

Chemical extraction and HPLC-HRMS analysis. For chemical extractions, amoeba cells at a start density of $3 \times 10^5$ cell/mL were grown in liquid cultures for 3 days at 22° C. under shaking conditions. Cultures were extracted twice with equal volume of ethyl acetate. The organic phases were dried with sodium sulfate and concentrated under reduced pressure using a rotary evaporator (Buechi). Crude extracts were dissolved in methanol and filtered through a 0.2 μm PTFE filter (Carl Roth). For detection of secondary metabolites, high-performance liquid chromatography (HPLC) analyses were performed using a Shimadzu LC-20AD instrument, equipped with a reverse-phase Kinetex C18 column (4.6×250 mm, 5 μm, 100 Å, Phenomenex) maintained at 30° C. A volume of 10 μL was injected using an autosampler and separated by applying a linear gradient of solvents A (water, 0.1% formic acid) and B (acetonitrile) at a flow rate of 0.8 mL/min: 10% B for 1 min, a linear increase to 95% B for 23 min, followed by column rinsing with 95% B for 10 min and re-equilibration with 10% B for 10 min. Organic compounds were detected by monitoring the absorbance at 280 and 400 nm using a PDA detector (Shimadzu). High-resolution mass spectrometry (HRMS)

was performed on a Q-Exactive Plus Hybrid Quadrupole Orbitrap mass spectrometer using electrospray ionization and an UltiMate 3000 UHPLC system (Thermo Fisher) equipped with a Kinetex C18 column (2.1×150 mm, 2.5 μm, 100 Å, Phenomenex). UHPLC was performed with an injection volume of 3 μL and a gradient elution of solvents A (water, 0.1% formic acid) and B (acetonitrile) at a flow rate of 0.3 mL/min: 5% B for 0.5 min, a linear gradient to 97% B for 11.5 min, then 97% B for 3 min and 5% B for 3 min. To quantify OA titers in culture extracts, the areas under the curve (AUCs) from extracted ion chromatograms were determined. The concentration was calculated by using a standard curve recorded with the pure reference compound.

Metabolic analysis of fruiting bodies. For inducing the development of amoeba, the protocol was performed as previously reported (16). Briefly, amoeba cells were pelleted from mid-log phase ($2-5 \times 10^6$ cells/mL) by centrifugation for 5 min at 500×g and 4° C. The cells were washed twice in ice-cold development buffer (5 mM $Na_2HPO_4$, 5 mM $KH_2PO_4$, 1 mM $CaCl_2$, 2 mM $MgCl_2$, pH 6.5) and re-suspended at a concentration of $2-3 \times 10^8$ cells/mL. For metabolic analysis of mature fruiting bodies, $8 \times 10^8$ cells were spread on KK2 plates and incubated at 22° C. for 26 h. The cell aggregates were scraped off, re-suspended in development buffer, freeze-dried and extracted with methanol. The liquid phase was separated by centrifugation and concentrated under reduced pressure. Crude extracts were analyzed by HR-MS as already described.

Isotope labeling studies. For the feeding experiments, 6 mM sodium $[1,2-^{13}C_2]$acetate (Merck) was added to the appropriate overexpression strains as indicated. Separate growth experiments were performed without the addition of acetate as precursor. After 3 days of growth, the cultures were extracted and analyzed for their metabolic profile by HR-MS as described.

PCP isolation, purification and NMR analysis. For NMR analysis, a 2 L large-scale culture was inoculated with $3 \times 10^5$ cells/mL of the pks37 overexpression mutant and extracted as described above. For pre-purification, the dried extract was dissolved in 6 mL of 50% methanol and loaded onto a Chromabond C18 SPE column (Macherey-Nagel) that was pre-equilibrated with 2 column volumes (CVs) of methanol followed by 1 CV water. After washing the column with 1 CV of water and 1.5 CVs of 30% methanol, the sample was eluted using 1 CV of 100% methanol. The collected methanol fraction was concentrated under reduced pressure to 1.5 mL and separated by semi-preparative HPLC using a Shimadzu LC-20AD instrument, equipped with a reverse-phase Kinetex C18 column (10×250 mm, 5 μm, 100 Å, Phenomenex) maintained at 30° C. Extracts were fractionated by using a linear gradient of solvents A (water, 0.1% formic acid) and B (acetonitrile) at a flow rate of 2 mL/min under the following conditions: 10% B for 1 min, a linear increase to 60% B for 14 min, held at 60% B for 15 min, increase to 97% for 1 min, followed by column rinsing with 97% B for 10 min, decrease to 10% in 2 min and re-equilibration with 10% B for 10 min. Organic compounds were detected by monitoring the absorbance at 254 and 280 nm using a PDA detector (Shimadzu). Collected fractions were evaporated using the Genevac EZ-2 sample concentrator (SP Scientific). Nuclear magnetic resonance (NMR) measurements ($^1$H, $^{13}$C, DEPT) were performed in deuterated methanol (VWR) on a Bruker Avance III 500 MHz spectrometer. The chemical shifts are reported in ppm relative to the solvent residual peak (δ (CD$_3$OD)=3.31 (49.05) ppm). The purified compound was used as a reference for further metabolic analyses.

Lab-scale fermentation of the pks5-oex strain. For upscaling the polyketide production, 5 L of HL5 medium supplemented with 10 g/L glucose and 10 µg/mL G418 were inoculated with 1×10$^6$ cells/mL of the pks5-oex strain and grown in a 7 L-stirred tank reactor (Sartorius) as a batch culture. To ensure fully aerated and oxygen unlimited conditions at all time, the level of dissolved oxygen tension (DOT) was controlled in cascade mode at a value of 20% by increasing the gas flow rate to a maximum value of 4 L/min followed by an increase of the stirring rate to a maximum value of 307 rpm. This aeration strategy was conducted to keep the hydro-mechanically stress on the cells to a minimum level. The pH was adjusted to 6.5 by addition of sulfuric acid if necessary. The batch culture was grown for 4 days at a constant temperature of 22° C.

Purification and NMR analysis of PKS5-derived metabolites. After fermentation of the pks5-oex strain, the culture was centrifuged for 20 min at 1,000×g and the supernatant was extracted twice with an equal volume of ethyl acetate. The organic phase was dried with sodium sulfate and concentrated to dryness under reduced pressure. The pellet was lyophilized and extracted with 800 mL methanol for 1 h. Then, the methanol extract was filtered and concentrated under reduced pressure. The crude extracts were dissolved in methanol and the compounds were isolated by preparative HPLC (Jasco), equipped with a reverse-phase Eurospher E C18 column (32×240 mm, 10 µm, 100 Å, Knauer). The extract was fractionated by using a linear gradient of solvents A (water, 0.1% formic acid) and B (acetonitrile) at a flow rate of 20 mL/min under the following conditions: 10% B for 1 min, a linear increase to 95% B for 24 min, held at 95% B for 10 min and re-equilibration with 10% B. Organic compounds were detected by monitoring the absorbance at 400 nm using a PDA detector (Jasco). Fractions showing an absorption maximum at 400 nm were combined, evaporated, dissolved in methanol and further purified by semi-preparative HPLC as described above, except the following changes in the gradient: 10% B for 1.5 min, a linear increase to 95% B for 38.5 min, followed by column rinsing with 95% B for 12 min, decrease to 10% in 3 min and re-equilibration with 10% B for 12 min. Collected fractions were evaporated and dissolved in deuterated DMSO (VWR). NMR spectra ($^1$H, $^{13}$C, DEPT, COSY, HSQC, HMBC) were recorded on a Bruker Avance III 600 MHz spectrometer. Chemical shifts are reported in ppm relative to the solvent residual peak (δ (DMSO-d$_6$)=2.50 (39.52) ppm).

Growth and metabolic activity monitoring. For determining the respiration activity, the D. discoideum pChR2, pChR5 and pChR7 strains were grown at an initial density of 1×10$^6$ cells/mL of HL5 medium supplemented with 1% [w/v] glucose and 20 µg/mL G418 in the presence or absence of 20 µg/mL doxycycline and 1 mM hexanoic acid as indicated. The respiration activity was measured by using the Kuhner TOM (transfer-rate online measurement) system equipped with oxygen partial pressure sensors and infrared sensors to calculate the oxygen transfer rate (OTR) and the carbon dioxide transfer rate (CTR). The cultures were grown in 250 mL TOM flasks for 144 h at 140 rpm and 22° C. without interruption to allow a constant OTR assessment. A filling volume of 52 mL was calculated in order to allow a maximum OTR of 8.5 mmol/L/h43, similar to culture conditions of previous experiments using 25 mL per 100 mL Erlenmeyer shake flasks.

For offline analysis, the strains were grown in parallel in 100 mL shake flasks filled with 25 mL liquid cultures, inoculated from the same master mix. At the indicated time points, 20 mL of each culture flask were harvested for chemical extraction and OA quantification by HR-MS as already described.

TABLE 1

| No | Primer Name | DNA Sequence (5' → 3') |
|---|---|---|
| | | Oligonucleotides as used. |
| 1 | pTX-37_F | AAAAATAAAAATCAGATCCAAGCTTAAAAAATGA ACAACAACAAAAGTATAAAC (SEQ ID NO: 1) |
| 2 | pTX-37_R | AACTCCAGTGAAAAGTTCTTCTCCTTTACTTTTAA TTAATTTAAATAAAATTGC (SEQ ID NO: 2) |
| 3 | pTX-GFP-lin_F | AGTAAAGGAGAAGAACTTTTCACTGGA (SEQ ID NO: 3) |
| 4 | pTX-lin_R | TTTTTAAGCTTGGATCTGATTTTTATTTTT (SEQ ID NO: 4) |
| 5 | pTX-37_R2 | GAATTCCTGCAGCCCGGGGGATCGTCTAGATTATT TAATTAATTTAAATAAAAT (SEQ ID NO: 5) |
| 6 | 37/pTX_F | AAATTAATTAAATAATCTAGACGATCCCCCGGGC TG (SEQ ID NO: 6) |
| 7 | 37/pTX_R | TTTGTTGTTGTTCATTTTTTAAGCTTGGATCTGAT TTTTATTTTT (SEQ ID NO: 7) |
| 8 | pTX-lin_F | TCTAGACGATCCCCCGGG (SEQ ID NO: 8) |
| 9 | pTX-1_F | AAAAATAAAAATCAGATCCAAGCTTAAAAAATGA ATAAAAATTCAAAAATCCAATCA (SEQ ID NO: 9) |
| 10 | pTX-1_R | GAATTCCTGCAGCCCGGGGGATCGTCTAGATTAG ACAACATTTTTTAAGAAACAACC (SEQ ID NO: 10) |
| 11 | pTX-5_F | AAAAATAAAAATCAGATCCAAGCTTAAAAAATGG ATATGAAATTAAATGATATTGAA (SEQ ID NO: 11) |
| 12 | pTX-5_R | GAATTCCTGCAGCCCGGGGGATCGTCTAGATTATT TATTTATCTTTTTCAAAAAATTTAA (SEQ ID NO: 12) |
| 13 | pTX-13_F | AAAAATAAAAATCAGATCCAAGCTTAAAAAATGG AAAACTTTAAATATAGAAATAATG (SEQ ID NO: 13) |
| 14 | pTX-13_R | GAATTCCTGCAGCCCGGGGGATCGTCTAGATTATT CTTGGCTTTGAACTT (SEQ ID NO: 14) |
| 15 | VINST1/pTX_F | ACGGTTACAAATTAATCTAGACGATCCCCCGGGC TG (SEQ ID NO: 15) |
| 16 | VINST1/pTX_R | CTCAACTGAAGCCATTTTTTAAGCTTGGATCTGAT TTTTATTTTT (SEQ ID NO: 16) |
| 17 | pTX-VINST1_F | AAAAATAAAAATCAGATCCAAGCTTAAAAAATGG CTTCAGTTGAGGAATTTAGA (SEQ ID NO: 17) |
| 18 | pTX-VINST1_R | GAATTCCTGCAGCCCGGGGGATCGTCTAGATTAA TTTGTAACCGTAGGAACGCT (SEQ ID NO: 18) |
| 19 | pV2AT-fadK_F | GGCGACGTTGAAGAAACCCTGGCCCTGATATGC ATCCCACAGGCCCGCAT (SEQ ID NO: 19) |
| 20 | pV2AT-fadK_R | CATCGCACCTTGAAAATAAAGATTTTCGATTTCAA TCTCTTCACAGACATCCTGCGTTAAACG (SEQ ID NO: 20) |

TABLE 1-continued

Oligonucleotides as used.

| No | Primer Name | DNA Sequence (5' → 3') |
|---|---|---|
| 21 | pV2AT-OLS_F | GGCGACGTTGAAGAAAACCCTGGCCCTGATATGA ATCATCTTCGTGCTGAGGGT (SEQ ID NO: 21) |
| 22 | pV2AT-OLS_R | CATCGCACCTTGAAAATAAAGATTTTCGATATATT TGATGGGAACACTACGCAC (SEQ ID NO: 22) |
| 23 | pV2AT-OAC_F2 | GGCGACGTTGAAGAAAACCCTGGCCCTGATATGG CAGTGAAGCATTTGATTGTATTGAAG (SEQ ID NO: 23) |
| 24 | pV2AT-OAC_R2 | CATCGCACCTTGAAAATAAAGATTTTCGATCTTTC GTGGTGTGTAGTCAAAAATGAGAAG (SEQ ID NO: 24) |
| 25 | TRE-VenusN_F | TAAATTAAATTAAATAAAAAATAAAAATCAAAAA AATGGATAAAGCGGAATTAATTCCC (SEQ ID NO: 25) |
| 26 | Tact8-VenusC_R | TTAAATAATTTATTTATTTAACTAGTACTACTACT TGTACAGCTCGTCCA (SEQ ID NO: 26) |
| 27 | pDM-TEVsite-lin_F | ATCGAAAATCTTTATTTTCAAGGTGCGATGG (SEQ ID NO: 27) |
| 28 | pDM-ZraI-lin_R | GTCGCCGTCAAGCTCGAC (SEQ ID NO: 28) |
| 29 | OLS-seq_F | GTGGAGCACGAGATGCAAACT (SEQ ID NO: 29) |
| 30 | fadK-XbaI-2A_R | CGGGCCTGTGGGATGCATTCTAGATCAGGGCCA (SEQ ID NO: 30) |
| 31 | pV2AT-37_F | GGCGACGTTGAAGAAAACCCTGGCCCTGATATGA ACAACAACAAAGTATAAACGATTTAAG (SEQ ID NO: 31) |
| 32 | 37-A_R | AAACTCATCTTGTAAAATTGGTGAAATTTCATAAA TTACTGTTGC (SEQ ID NO: 32) |
| 33 | 37-B_R | AGCACGAAGATGATTAATTGGTGAAATTTCATAA ATTACTGTTGC (SEQ ID NO: 33) |
| 34 | 37-C_R | GGCGGTGCCAATGGCATCGTTATCACTATTATTAT CTTCTGATATTATTGG (SEQ ID NO: 34) |
| 35 | OLS-A_F | GAAATTTCACCAATTTTACAAGATGAGTTTCCTGA CTACT (SEQ ID NO: 35) |
| 36 | OLS-B_F | GAAATTTCACCAATTAATCATCTTCGTGCTGAGGG T (SEQ ID NO: 36) |
| 37 | OLS-C_F | AATAGTGATAACGATGCCATTGGCACCGCCAAT (SEQ ID NO: 37) |
| 38 | OLS-seq_R | GATGGCCTTTGCACAAGCATC (SEQ ID NO: 38) |
| 39 | 37PP-S2458A_F | GACTATGGTTTAGATGCATTACTATCAAGTGAATT ATCA (SEQ ID NO: 39) |
| 40 | 37PP-S2458A_R | CACTTGATAGTAATGCATCTAAACCATAGTCACTA AATG (SEQ ID NO: 40) |
| 41 | pDM-B_DD-lin_F | GGAGAAAGCTTGTTTAAGGGGCC (SEQ ID NO: 41) |
| 42 | pDM-B_DD-lin_R | AGCTCTGAGATGGTTAATTGGTGAAATTTCATAA ATTACTGTTGCCA (SEQ ID NO: 42) |
| 43 | OLS-DD_F | GAAATTTCACCAATTAACCATCTCAGAGCTGAAG GAC (SEQ ID NO: 43) |
| 44 | OLS-DD_R | ATATTTAATTGGAACTGATCTAACAACAACTC (SEQ ID NO: 44) |

TABLE 1-continued

Oligonucleotides as used.

| No | Primer Name | DNA Sequence (5' → 3') |
|---|---|---|
| 45 | OAC-DD_F | GAGTTGTTGTTAGATCAGTTCCAATTAAATAT (SEQ ID NO: 45) |
| 46 | OAC-DD_R | ATCACGCGGCCCCTTAAAC (SEQ ID NO: 46) |
| 47 | OLS-DD_R2 | GGATCGTCTAGATTAATATTTAATTGGAACTGATC TAACAACAACTC (SEQ ID NO: 47) |
| 48 | OLS-DD/pTX_F | GTTCCAATTAAATATTAATCTAGACGATCCCCCGG G (SEQ ID NO: 48) |
| 49 | pks37_NB_F1 | GCCATTAGATTCATGTCATCCGGTAATC (SEQ ID NO: 49) |
| 50 | pks37_GenR2 | GCCATACCAACATCAGGTATAGAAGC (SEQ ID NO: 50) |

PCP Production by Overexpression of Pks37 in *D. discoideum*

As a proof-of-concept study, the inventors first overexpressed the PKS37 encoding gene (pks37 or also named stlB) in *D. discoideum*. Gene activation was achieved by expressing pks37 under the control of a constitutive actin15 promoter, either alone or as a pks37-GFP fusion construct, of which the latter was used solely for expression analysis (FIG. 1B). Transcription of the untagged construct was verified by northern blot analysis (FIG. 1C). After growth at 22° C. for three days, total metabolites from the wild-type and pks37 overexpression (pks37-oex) strains were extracted and analyzed. The resulting metabolic profile showed a main peak that was neither present in the wild-type nor in the GFP-tagged mutant (FIG. 1D), suggesting that PKS37 completely lost its enzymatic activity when tagged with GFP. The PKS37-derived compound was purified from a large-scale culture by solid phase extraction followed by preparative HPLC. Subsequent HR-MS analysis revealed the presence of a compound with the m/z of 223.0965 [M−H]⁻ (1) in the negative mode. The detected m/z for compound 1 corresponds to the mono-isotopic mass of 224.1048 and NMR structure elucidation confirmed its identity as PCP. Additional feeding experiments using [1,2-$^{13}$C$_2$]acetate followed by MS measurements revealed a full incorporation of six acetate units into PCP further proving its polyketide origin from PKS37.

Since PCP is the precursor for the DIF-1 biosynthesis (19) (FIG. 1E), the inventors also investigated the presence of DIF-1 and its halogenated intermediates, chloro- and dichloro-PCP, during vegetative growth. However, none of them were detected under these conditions. In contrast, the extraction and metabolic analysis of mature fruiting bodies allowed the detection of sequential chemical modifications during DIF-1 biosynthesis starting from PCP (FIG. 1F).

Secondary Metabolite Production by Amoeba PKSs

Since overexpression of pks37 resulted in a high-level polyketide production in vivo, the inventors decided to further investigate the natural product potential of *D. discoideum* by expression of still uncharacterized PKS genes. Under vegetative growth conditions, the newly generated overexpression mutants were cultured for three days, extracted and analyzed by HPLC and HR-MS. The extracted ion chromatogram of the pks5-oex mutant revealed multiple peaks with the same mass in the positive mode suggesting the presence of different structural isomers. In order to obtain the PKS5-derived metabolites in a sufficient amount for structure elucidation, the inventors performed a lab-scale fermentation and compound purification using preparative HPLC. The NMR-guided structure elucidation showed the presence of an unsaturated long-chain fatty acid (C18) containing a secondary hydroxyl group at carbon 17, and a gamma or alpha methyl group. The newly identified molecules were named Dictyodene B and A, with the m/z of 301.1792 $[M+H]^+$ (5) and 301.1787 $[M+H]^+$ (6), respectively (FIG. 2A). The fatty acid skeleton proves the polyketide origin of the molecule, whereby the methyl group is most likely introduced by the predicted methyltransferase domain of PKS5 (11).

For the pks13-oex strain, the HPLC chromatogram showed two peaks at the retention time of 21.7 and 23.2 min, whereby subsequent HR-MS analysis identified ions with the m/z of 283.1340 $[M−H]^+$ (7) and 311.1641 $[M+H]^+$ (8), respectively (FIG. 2A). The identity of the PKS13-derived metabolites remains to be elucidated. Furthermore, the inventors also analyzed the well described PKS1 since previous in vitro studies proposed 4-methyl-5-pentylbenzene-1,3-diol (MPBD) as the polyketide product (14, 15). The metabolic analysis of the pks1-oex strain revealed a main peak with the m/z of 195.1379 $[M+H]^+$ (9) in the positive mode (FIG. 2B), confirming MPBD as the main polyketide product in vivo.

These data give further evidence that the here developed homologous expression system makes D. discoideum an optimal platform for the functional analysis of PKS genes. It enables the inventors to confirm the production of suspected polyketides in vivo, and even more relevant, to elucidate novel natural products of polyketide origin.

Functional Expression of a Plant Type III PKS in D. discoideum

Since PKS37 contains a C-terminal type III PKS domain, the inventors investigated the potential of amoebae to functionally express a stand-alone plant type III PKS (FIG. 3A). Coumaroyl-CoA is a widely spread starter unit of several type III PKSs and the presence of three gene copies encoding a p-coumaroyl-CoA ligase in D. discoideum (Gene ID: 8624748-50) suggested the amoeba as a suitable host for producing plant polyketides from plant type III PKSs, that catalyze the condensation of p-coumaroyl-CoA and malonyl-CoA units for the polyketide biosynthesis.

The inventors first aimed to produce resveratrol, a stilbene that is mainly present in grapes, peanuts and a variety of berries, and known for its antioxidant, anti-tumorigenic and anti-inflammatory properties (20). The inventors heterologously expressed the stilbene synthase (STS) encoding gene from the grapevine Vitis vinifera under control of the constitutively active actin15 promoter. The STS overexpression strain was grown as a liquid culture supplemented with p-coumaric acid for three days and analyzed for metabolite production by HR-MS. The inventors confirmed the heterologous production of cis-resveratrol (11) in D. discoideum (FIG. 3B), without co-expression of any additional coumaroyl-CoA ligase encoding gene. However, cis-resveratrol could also be detected in small quantities in the wild-type strain upon feeding of external p-coumaric acid, suggesting that the amoeba itself expresses one or more enzymes with residual stilbene synthase activity.

Heterologous Production of Olivetolic Acid in Amoeba

The heterologous production of resveratrol suggested that the amoeba can potentially be used as a chassis for the production of plant metabolites. To further explore this, the inventors decided to produce an additional polyketide, the olivetolic acid (OA), which is a major intermediate in the cannabinoid biosynthetic pathway of Cannabis sativa. Remarkably, the PCP of D. discoideum and OA from C. sativa are both synthesized from hexanoyl starter molecules and also share the malonyl-CoA derived aromatic ring.

The inventors designed a biosynthetic pathway for the production of OA built on the medium-chain fatty acid CoA ligase FadK of E. coli (21), and the C. sativa enzymes olivetol synthase (OLS) and olivetolic acid cyclase (OAC, FIG. 4A) (9, 10). FadK acts as medium-chain fatty acid CoA ligase that can activate hexanoic acid to hexanoyl-CoA following its uptake as an externally provided precursor (21). OLS and OAC subsequently condense the hexanoyl-CoA starter molecule with three internally provided malonyl-CoA units and cyclize the tetraketide to form OA. In order to express all required genes in D. discoideum, a multi-gene expression vector was established based on the previously reported pV2A-T system (22) and an amoeba expression vector containing an inducible, tetracycline-controlled $Tet^{ON}$ promoter. Transcription of the OA biosynthetic cluster yielded a single polycistronic mRNA. Each gene was spaced by viral 2A sequences leading to the translation of separate proteins with the 2A peptides being removed by a co-expressed Tobacco etch virus (TEV) peptidase (FIG. 4B). The inventors generated two strains expressing different polycistronic constructs: pChR1 comprised the biosynthetic genes of the OA pathway alone, while pChR2 expressed the same genes and the TEV. Expression in pChR1 allowed immunodetection of the proteins due to the presence of the 2A peptide sequences, and expression was verified by western blot analysis using anti-2A antibodies (FIG. 4C). Strain pChR2 expressed the tag-free enzymes and was used for metabolic analysis. HR-MS data of culture extracts from the pChR2 strain revealed that the presence of the polycistronic construct alone was not sufficient for the heterologous OA biosynthesis. Instead, supplementation of hexanoic acid to the growth medium led to OA production in the amoeba (FIG. 4D). These data shows that D. discoideum can serve as an alternative chassis for the heterologous production of eukaryotic metabolites. However, the need of external hexanoic acid revealed that the carboxylic acid arsenal of this organism is quite limited and required precursor supplementation and the co-expression of an ad hoc CoA ligase.

Construction of an Inter-Kingdom PKS Hybrid for OA Biosynthesis

To circumvent the need for external supplements and directly produce OA in D. discoideum from primary metabolic precursors, the inventors modified the biosynthetic pathway by taking advantage of PKS37 as a hybrid of a FAS and a PKS III domain. Here, the FAS domain synthesizes a hexanoyl moiety, which is then transferred to the PKS III domain for PCP biosynthesis. By swapping the PKS III domain with the OLS of C. sativa, the inventors expected that the amoeba FAS domain could directly provide the hexanoyl-intermediate to OLS leading to the formation of the tetraketide intermediate (FIG. 5A). To test this hypothesis, three different domain swapping constructs were generated (FIG. 5B). The inventors first designed an alignment-based construct (pChR3), in which the PKS III domain of PKS37 (2619-2968 aa) was exchanged with the conserved region of the OLS starting from L25 (25-385 aa). A second construct was generated (pChR4) based on swapping both PKS III domains starting from the predicted N-terminal ß-sheets (PKS37: 2606-2968 aa replaced by OLS: 14-385 aa). In addition, the inventors created a fusion construct (pChR5), in which the complete PKS III domain of PKS37 (2619-2968 aa) was exchanged by the OLS (2-385 aa). Each construct was co-expressed with genes encoding the C.

*sativa* OAC and the TEV peptidase as a polycistron, separated by 2A sequences. While the first two constructs did not yield in any OA production, HR-MS data revealed that expression of the pChR5 hybrid indeed led to the production of the plant-derived polyketide without any precursor supplementation (FIGS. 5B and 5D). This shows that the complete domain architectures of both catalytic subunits were necessary to generate a functional amoeba FAS-plant PKS III hybrid.

To exclude another intracellular source of the starter unit and proof that the hexanoyl-intermediate was solely provided via the PKS37/FAS domain, the inventors additionally created a loss-of-function mutant of the pChR5 hybrid strain by introducing a S2458A substitution in the phosphopantetheine-binding site of the FAS-ACP domain (pChR6). Similar transcription levels of the functional pChR5 hybrid and its loss-of-function mutant pChR6 were verified by northern hybridization (FIG. 5C). The absence of OA formation in the loss-of-function mutant shows evidence that the hexanoyl precursor is exclusively provided by the PKS37/FAS domain (FIG. 5D). Moreover, the lack of a thioesterase domain in the PKS37 amino acid sequence, and HR-MS data showing no traces of free hexanoic acid in the pChR5 strain, strongly suggest that the hexanoyl moiety moves directly from the FAS to the PKS III domain without leaving the enzyme. To further improve the OA production, the OLS and OAC genes of the functional pChR5 hybrid vector were replaced with their codon-optimized version for *D. discoideum*, resulting in the pChR7 strain. In addition, the codon-optimized hybrid gene was expressed without the OAC under control of the constitutively active actin15 promoter (pChR8 strain) to analyze the OA and shunt product formation (FIG. 6). In absence of the OAC, the PKS37/FAS-OLS enzyme is proposed to produce olivetol and two α-pyrones, namely pentyl diacetic acid lactone (PDAL) and hexanoyl triacetic acid lactone (HTAL) as catalytic by-products. HR-MS data indicate the presence of all shunt products in both strains, whereby a higher abundance of α-pyrones is detectable in the pChR8 strain. Although traces of OA can also be observed in the pChR8 strain, the induced pChR7 strain shows a clear shift of the chemical equilibrium from α-pyrones towards OA formation. These results demonstrate that the engineered synthetic hybrid shows the same product profile as reported for the original OLS (10).

For further evidence of the functional involvement of PKS37/FAS in OA biosynthesis, the optimized pChR7 hybrid and the fadK containing pChR2 strain were grown in medium enriched with $[1,2\text{-}^{13}C_2]$acetate and analyzed for their metabolic profile by HR-MS (FIG. 7). The pChR2 strain, supplemented with hexanoic acid and labeled acetate, showed the incorporation of only three acetate units into OA, as indicated by a 6-mass unit shift of the molecular ion of OA. This suggests that the labeled malonyl-CoA building blocks are used by the OLS to synthesize the benzoyl group, while the hexanoyl-moiety is clearly derived from the externally provided hexanoic acid. In contrast, the HR-MS analysis of the pChR7 hybrid, supplemented with labeled acetate, shows a pattern as expected for a completely acetate-derived polyketide indicating a full incorporation of six acetate units into OA. This indeed proves the function of the PKS37/FAS domain to provide the hexanoyl-precursor for the OA and PCP biosynthesis directly from acetate units.

Taken together, the inventors report here the first synthetic inter-kingdom hybrid enzyme that enables OA biosynthesis exclusively from acetyl- and malonyl-CoA.

Growth and Metabolic Activity of OA Production Strains

We compared the growth and metabolic activities of the pChR5 hybrid, the codon-optimized pChR7 hybrid, and the fadK expressing pChR2 strain requiring hexanoic acid supplementation in real-time (FIG. 8). After a lag phase of approximately 24 h, the oxygen transfer rate (OTR) increased exponentially and reached the maximum of 5.6 mmol/L/h after 91 h for the induced pChR7 strain, slightly lower than the maximum OTR for all remaining strains (6.3 mmol/L/h) (FIG. 8A). Supplementation of the pChR2 strain with 1 mM hexanoic acid did not change the maximum OTR, but led to a delayed exponential increase that peaked after 92 h (instead of 77 h) and revealed an initial growth inhibitory effect of the precursor (FIG. 8A). Although the induced pChR7 strain shows the lowest metabolic activity, the OA production yielded in 4.5 μg/L after 96 h, while the pChR5 hybrid and supplemented pChR2 strain reached only 3.2 and 3.5 μg/L, respectively (FIG. 8B).

REFERENCES AS CITED

1 Austin, M. B. & Noel, J. P. The chalcone synthase superfamily of type III polyketide synthases. *Nat Prod Rep* 20, 79-110, doi:10.1039/b100917f (2003).

2 Lim, Y. P., Go, M. K. & Yew, W. S. Exploiting the Biosynthetic Potential of Type III Polyketide Synthases. *Molecules* 21, doi:10.3390/molecules21060806 (2016).

3 Hertweck, C. The biosynthetic logic of polyketide diversity. *Angew Chem Int Ed Engl* 48, 4688-4716, doi:10.1002/anie.200806121 (2009).

4 Morita, H., Wong, C. P. & Abe, I. How structural subtleties lead to molecular diversity for the type III polyketide synthases. *The Journal of biological chemistry* 294, 15121-15136, doi:10.1074/jbc.REV119.006129 (2019).

5 Herbst, D. A., Townsend, C. A. & Maier, T. The architectures of iterative type I PKS and FAS. *Nat Prod Rep* 35, 1046-1069, doi:10.1039/c8np00039e (2018).

6 Chen, A., Re, R. N. & Burkart, M. D. Type II fatty acid and polyketide synthases: deciphering protein-protein and protein-substrate interactions. *Nat Prod Rep* 35, 1029-1045, doi:10.1039/c8np00040a (2018).

7 Keller, N. P. Fungal secondary metabolism: regulation, function and drug discovery. *Nat Rev Microbiol* 17, 167-180, doi:10.1038/s41579-018-0121-1 (2019).

8 Shimizu, Y., Ogata, H. & Goto, S. Type III Polyketide Synthases: Functional Classification and Phylogenomics. *Chembiochem* 18, 50-65 (2017).

9 Taura, F. et al. Characterization of olivetol synthase, a polyketide synthase putatively involved in cannabinoid biosynthetic pathway. *FEBS Lett* 583, 2061-2066, doi:10.1016/j.febslet.2009.05.024 (2009).

10 Gagne, S. J. et al. Identification of olivetolic acid cyclase from *Cannabis sativa* reveals a unique catalytic route to plant polyketides. *Proc Natl Acad Sci USA* 109, 12811-12816, doi:10.1073/pnas.1200330109 (2012).

11 Eichinger, L. et al. The genome of the social amoeba *Dictyostelium discoideum*. *Nature* 435, 43-57, doi:10.1038/nature03481 (2005).

12 Heidel, A. J. et al. Phylogeny-wide analysis of social amoeba genomes highlights ancient origins for complex intercellular communication. *Genome Res* 21, 1882-1891, doi:10.1101/gr.121137.111 (2011).

13 Zucko, J. et al. Polyketide synthase genes and the natural products potential of *Dictyostelium discoideum*. *Bioinformatics* 23, 2543-2549, doi:10.1093/bioinformatics/btm381 (2007).

14 Ghosh, R. et al. Dissecting the functional role of polyketide synthases in *Dictyostelium discoideum*: biosynthesis of the differentiation regulating factor 4-methyl-5-pentylbenzene-1,3-diol. *The Journal of biological chemistry* 283, 11348-11354, doi:10.1074/jbc.M709588200 (2008).

15 Austin, M. B. et al. Biosynthesis of *Dictyostelium discoideum* differentiation-inducing factor by a hybrid type I fatty acid-type III polyketide synthase. *Nat Chem Biol* 2, 494-502, doi:10.1038/nchembio811 (2006).

16 Fey, P., Kowal, A. S., Gaudet, P., Pilcher, K. E. & Chisholm, R. L. Protocols for growth and development of *Dictyostelium discoideum*. *Nat Protoc* 2, 1307-1316, doi: 10.1038/nprot.2007.178 (2007).

17 Morris, H. R., Taylor, G. W., Masento, M. S., Jermyn, K. A. & Kay, R. R. Chemical structure of the morphogen differentiation inducing factor from *Dictyostelium discoideum*. *Nature* 328, 811-814, doi:10.1038/328811a0 (1987).

18 Kay, R. R. & Jermyn, K. A. A possible morphogen controlling differentiation in *Dictyostelium*. *Nature* 303, 242-244, doi:10.1038/303242a0 (1983).

19 Kay, R. R. The biosynthesis of differentiation-inducing factor, a chlorinated signal molecule regulating *Dictyostelium* development. *The Journal of biological chemistry* 273, 2669-2675, doi:10.1074/jbc.273.5.2669 (1998).

20 Salehi, B. et al. Resveratrol: A Double-Edged Sword in Health Benefits. *Biomedicines* 6, doi:10.3390/biomedicines6030091 (2018).

21 Morgan-Kiss, R. M. & Cronan, J. E. The *Escherichia coli* fadK (ydiD) gene encodes an anerobically regulated short chain acyl-CoA synthetase. *J Biol Chem* 279, 37324-37333, doi:10.1074/jbc.M405233200 (2004).

22 Hoefgen, S. et al. Facile assembly and fluorescence-based screening method for heterologous expression of biosynthetic pathways in fungi. *Metab Eng* 48, 44-51, doi:10.1016/j.ymben.2018.05.014 (2018).

23 Neumann, C. S., Walsh, C. T. & Kay, R. R. A flavin-dependent halogenase catalyzes the chlorination step in the biosynthesis of *Dictyostelium* differentiation-inducing factor 1. *Proc Natl Acad Sci USA* 107, 5798-5803, doi: 10.1073/pnas.1001681107 (2010).

24 Palmer, C. M. & Alper, H. S. Expanding the Chemical Palette of Industrial Microbes: Metabolic Engineering for Type III PKS-Derived Polyketides. *Biotechnol J*14, e1700463, doi:10.1002/biot.201700463 (2019).

25 Wang, S. et al. Metabolic engineering of *Escherichia coli* for the biosynthesis of various phenylpropanoid derivatives. *Metab Eng* 29, 153-159, doi:10.1016/j.ymben.2015.03.011 (2015).

26 Milke, L., Aschenbrenner, J., Marienhagen, J. & Kallscheuer, N. Production of plant-derived polyphenols in microorganisms: current state and perspectives. *Appl Microbiol Biotechnol* 102, 1575-1585, doi:10.1007/s00253-018-8747-5 (2018).

27 Unkles, S. E., Valiante, V., Mattern, D. J. & Brakhage, A. A. Synthetic biology tools for bioprospecting of natural products in eukaryotes. *Chem Biol* 21, 502-508 (2014).

28 Nair, D. R. et al. Two functionally distinctive phosphopantetheinyl transferases from amoeba *Dictyostelium discoideum*. *PLoS One* 6, e24262, doi:10.1371/journal.pone.0024262 (2011).

29 Bozzaro, S. The model organism *Dictyostelium discoideum*. *Methods Mol Biol* 983, 17-37, doi:10.1007/978-1-62703-302-2_2 (2013).

30 Vaknin, Y. et al. Identification and Characterization of a Novel *Aspergillus fumigatus* Rhomboid Family Putative Protease, RbdA, Involved in Hypoxia Sensing and Virulence. *Infect Immun* 84, 1866-1878, doi:10.1128/iai.00011-16 (2016).

31 Levi, S., Polyakov, M. & Egelhoff, T. T. Green fluorescent protein and epitope tag fusion vectors for *Dictyostelium discoideum*. *Plasmid* 44, 231-238, doi:10.1006/plas.2000.1487 (2000).

32 Fey, P., Dodson, R. J., Basu, S. & Chisholm, R. L. in *Dictyostelium discoideum Protocols* (eds Ludwig Eichinger & Francisco Rivero) 59-92 (Humana Press, 2013).

33 Veltman, D. M., Keizer-Gunnink, I. & Haastert, P. J. An extrachromosomal, inducible expression system for *Dictyostelium discoideum*. *Plasmid* 61, 119-125, doi: 10.1016/j.plasmid.2008.11.002 (2009).

34 Hirst, J., Kay, R. R. & Traynor, D. *Dictyostelium* Cultivation, Transfection, Microscopy and Fractionation. *Bio Protoc* 5, doi:10.21769/bioprotoc.1485 (2015).

The invention claimed is:

1. A hybrid protein comprising a polyketide synthase 37 (PKS37) having β-ketoacyl synthase activity and lacking a functional C-terminal type III PKS domain, and the hybrid protein comprising a functional plant olivetol synthase (OLS) or an active fragment thereof with olivetol synthase activity at C-terminus of the hybrid protein.

2. The hybrid protein according to claim 1, wherein said hybrid protein comprises amino acids 1 to 2618 of PKS37 from Dictyostelium discoideum as encoded by a polynucleotide amplifiable from genome of Dictyostelium discoideum AX2 using primer pair SEQ ID NOs: 31 and 32, and amino acids 2 to 385 of OLS from Cannabis sativa as encoded by a polynucleotide amplifiable from genome of Cannabis sativa using primer pair SEQ ID NOs: 36 and 38.

3. The hybrid protein according to claim 1, wherein said pks37 is from Dictyostelium discoideum.

4. A polynucleotide sequence that encodes the hybrid protein of claim 1.

5. The nucleotide sequence according to claim 4, wherein said hybrid protein comprises amino acids 1 to 2618 of PKS37 from Dictyostelium discoideum as encoded by a polynucleotide amplifiable from genome of Dictyostelium discoideum AX2 using primer pair SEQ ID NOs: 31 and 32, and amino acids 2 to 385 of OLS from Cannabis sativa as encoded by a polynucleotide amplifiable from genome of Cannabis sativa using primer pair SEQ ID NOs: 36 and 38.

6. A multi-gene expression vector for the recombinant production of olivetolic acid (OA) in a host species selected from amoebozoa, comprising and expressing genes that encode the hybrid protein according to claim 1, a plant olivetolic acid cyclase (OAC), and Tobacco etch virus (TEV) peptidase, wherein said genes are transcribed as a single polycistronic mRNA spaced apart by viral 2A sequences.

7. A method for the recombinant production of olivetolic acid (OA) in a species selected from amoebozoa, comprising the steps of a) culturing a recombinant amoebozoa species comprising and expressing the multi-gene expression vector according to claim 6 in a suitable culture medium without a need of hexanoic acid supplementation, and b) isolating said OA from said culture of step a).

8. A method for producing $\Delta^9$-tetrahydrocannabinol or another cannabinoid, comprising the steps of performing the method according to claim 7, and chemically and/or enzymatically converting the olivetolic acid (OA) as produced into $\Delta^9$-tetrahydrocannabinol or another cannabinoid.

9. The multi-gene expression vector according to claim 6, wherein said plant olivetol synthase (OLS) and/or plant olivetolic acid cyclase (OAC) is from C. sativa.

10. The multi-gene expression vector according to claim 6, wherein said genes are codon optimized for expression in said amoebozoa host species, wherein said species is Dictyostelium discoideum.

11. A recombinant amoebozoa host species, comprising and expressing the multi-gene expression vector according to claim 6.

* * * * *